United States Patent
Johnson et al.

(10) Patent No.: US 9,757,434 B2
(45) Date of Patent: Sep. 12, 2017

(54) FXA VARIANT COMPOSITIONS

(71) Applicant: PFIZER INC., New York, NY (US)

(72) Inventors: Keith A. Johnson, North Chelmsford, MA (US); Jason C. Rouse, Londonderry, NH (US); Penelope Jane Sharpe, Derry, NH (US); Stacey B. Weston, Dracut, MA (US); Michael Anthony Jankowski, Newbury, MA (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 14/495,478

(22) Filed: Sep. 24, 2014

(65) Prior Publication Data

US 2015/0182604 A1    Jul. 2, 2015

Related U.S. Application Data

(63) Continuation of application No. PCT/IB2014/064564, filed on Sep. 16, 2014.

(60) Provisional application No. 61/881,834, filed on Sep. 24, 2013.

(51) Int. Cl.
| C12M 1/20 | (2006.01) |
| A61K 38/48 | (2006.01) |
| A61K 38/36 | (2006.01) |
| C12N 9/64 | (2006.01) |

(52) U.S. Cl.
CPC .......... A61K 38/4846 (2013.01); A61K 38/36 (2013.01); C12N 9/6432 (2013.01)

(58) Field of Classification Search
None
See application file for complete search history.

(56) References Cited

U.S. PATENT DOCUMENTS

| | | | |
|---|---|---|---|
| 5,597,799 | A | 1/1997 | Wolf |
| 6,562,598 | B1 | 5/2003 | Himmelspach |
| 6,573,071 | B1 | 6/2003 | Himmelspach |
| 6,905,846 | B2 | 6/2005 | Himmelspach |
| 6,958,322 | B1 | 10/2005 | Himmelspach |
| 7,220,569 | B2 | 5/2007 | Himmelspach |
| 8,153,590 | B2 * | 4/2012 | Lu ............... A61K 38/4826 424/185.1 |
| 8,383,386 | B2 | 2/2013 | Camire |
| 8,436,144 | B2 | 5/2013 | Christophe |
| 8,455,439 | B2 | 6/2013 | Lu et al. |
| 9,347,051 | B2 | 5/2016 | Schulte |
| 9,371,522 | B2 | 6/2016 | Camire |
| 9,410,137 | B2 | 8/2016 | Camire |
| 2003/0138914 | A1 | 7/2003 | Himmelspach |
| 2003/0181381 | A1 | 9/2003 | Himmelspach |
| 2006/0148038 | A1 | 7/2006 | Louvain |
| 2009/0098119 | A1 | 4/2009 | Lu |
| 2009/0175828 | A1 | 7/2009 | Schulte et al. |
| 2009/0175931 | A1 | 7/2009 | Camire |
| 2011/0015128 | A1 | 1/2011 | Sinha et al. |
| 2014/0030247 | A1 | 1/2014 | Madison et al. |
| 2014/0050716 | A1 | 2/2014 | Polack |
| 2014/0120155 | A1 | 5/2014 | Camire |
| 2014/0248259 | A1 | 9/2014 | Camire |
| 2015/0343034 | A1 | 12/2015 | Pittman et al. |

FOREIGN PATENT DOCUMENTS

| | | |
|---|---|---|
| EP | 1539816 | 1/2006 |
| EP | 1728798 | 12/2006 |
| EP | 1820508 | 8/2007 |
| EP | 1948690 | 7/2008 |
| EP | 1991255 | 11/2008 |
| WO | 9838317 | 9/1998 |
| WO | 9838318 | 9/1998 |
| WO | 0170763 | 9/2001 |
| WO | 03035861 | 5/2003 |
| WO | 2004005347 | 1/2004 |
| WO | 2007059513 | 5/2007 |
| WO | 2007/096116 | 8/2007 |
| WO | 2007096116 | 8/2007 |
| WO | 2011/008885 | 1/2011 |
| WO | 2013049804 | 4/2013 |
| WO | 2014/018120 | 1/2014 |
| WO | 2014118677 | 8/2014 |
| WO | 2015066606 | 5/2015 |
| WO | 2015110939 | 7/2015 |

OTHER PUBLICATIONS

Jesty et al. (JBC, vol. 250, No. 12, Jun. 1975, pp. 4497-4504).*
Rezaie, A. R. and Esmon, C. T. (1995) Contribution of residue 192 in factor Xa to enzyme specificity and function. J. Biol. Chem. 270, 16176-16181.
Rezaie, A. R. and He, X. (2000) Sodium binding site of factor Xa: Role of sodium in the prothrombinase complex. Biochemistry 39, 1817-1825.
Rezaie, A. R., Neuenschwander, P.F., Morrissey, J.H., and Esmon, C.T. (1993) Analysis of the functions of the first epidermal growth factor-like domain of factor X. J. Biol. Chem. 268, 8176-8180.
Robison, D., Furie, B., Furie, B. C., and Bing, D. H. (1980) Active site of bovine factor X. Characterization using substituted benzamidines as competitive inhibitors and affinity-labeling reagents. J.Biol.Chem. 255, 2014-2021.
Rudinger, J. "Characteristics of the amino acids as components of a peptide hormone sequence." In Peptide Hormones (JA Parsons, ed.) University Park Press.1976:1-7.
Rudolph, A.E., et al., "Expression, purification, and characterization of recombinant human factor X." Protein Expr Purif, Aug. 1997;10(3):373-8.
Schlachterman, A et al., Factor V Leiden improves in vivo hemostasis in murine hemophilia models, J Thromb Haemost 3(12):2730-2737 (Dec. 2005).

(Continued)

*Primary Examiner* — Hope Robinson

(57) ABSTRACT

Compositions are provided comprising recombinant variants of the human clotting Factor Xa. Such compositions include a wide variety of isoforms and post-translational modifications of FXa and are useful for treating subjects in need of hemostasis.

45 Claims, 10 Drawing Sheets

(56) References Cited

OTHER PUBLICATIONS

Stanley, T. B., Humphries, J., High, K. A., and Stafford, D. W. (1999) Amino acids responsible for the reduced affinities of vitamin K-dependent propeptides for the carboxylase. Biochemistry 38, 15681-15687.
Stanley, T. B., Jin, D. Y., Lin, P., and Stafford, D. W. (1999) The propeptides of the vitamin K-dependent proteins possess different affinities for the vitamin K dependent carboxylase. J. Biol. Chem. 274, 16940-16944.
Strandberg, L., et al. "Variants of tissue-type plasminogen activator with substantially enhanced response and selectivity toward fibrin co-factors." J Biol Chem. Oct. 6, 1995;270(40):23444-9.
Sun, T., et al. "Vitamin K epoxide reductase significantly improves carboxylation in a cell line overexpressing factor X." Blood, 106(12):3811-3815 (2005).
Sziegoleit, A., A human pancreatic chymotrypsin: biochemical and molecular characterization, GenBank accession No. CAA74031.1, direct submission Jun. 10, 1997.
Tachias, K. and Madison, E. (1996) Converting tissue-type plasminogen activator into a zymogen. J.Biol.Chem. 271, 28749-28752.
Tachias, K. and Madison, E. (1997) Converting tissue type plasminogen activator into a zymogen. Important role of Lys156. J.Biol.Chem. 272, 28-31.
Thalji N., Patel-Hett S., Fruebis J., Pittman D., Camire R.M. Reversal of direct factor Xa inhibitors using factor Xa zymogen-like variants. Journal of Thrombosis and Haemostasis. 11 (pp. 167), Jul. 2013. Abstract from 24th Congress of the International Society on Thrombosis and Haemostasis.
Toso, R. et al. "Factor VII mutant V154G models a zymogen-like form of factor VIIa." The Biochemical Journal, 369(3):563-571 (Feb. 1, 2003).
Toso, R. et al. "Factor VII variants as tools to study Factor VIIa salt bridge formation." Database Biosis. Biosciences, Information Service, Philadelphia, PA & Blood, 98(11):526a (Nov. 16, 2001) [Abstract].
Toso, R. et al. "The conformational switch from the factor X zymogen to protease state mediates exosite expression and prothrombinase assembly." Journal of Biological Chemistry, 283(27):18627-18635 (Jul. 2008).
Toso, Raffaella; Zhu, Hua; Camire, Rodney M., Alteration of the factor X zymogen to protease transition provides evidence for allosteric linkage between the S1 and FVa binding sites. Blood. 106(11, Part 1). Nov. 16, 2005. Abstract from 2005 Annual Meeting of the American Society of Hematology.
Venkateswarlu, D., Perera, L., Darden, T., and Pedersen, L.G. (2002) Structure and dynamics of zymogen human blood coagulation factor X. Biophys. J. 82, 1190-1206.
Wells, JA "Additivity of mutational effects in proteins." Biochemistry. Sep. 18, 1990;29(37):8509-17.
Wolf, D.L., et al. "Design of Constructs for the Expression of Biologically Active Recombinant Human Factors X and Xa." J Biol Chem. Jul. 25, 1991;266(21):13726-13730.

Zhong, D., Bajaj, M. S., Sclunidt, A. E., and Bajaj, S. P. (2002) The N-terminal EGF-like domain in factor IX and factor X represents an important recognition motif for binding to tissue factor. J.Biol. Chem. 277, 3622-3631.
International Preliminary Report on Patentability (IPRP) PCT/IB2014/064564 (WO 2015/044836).
Written Opinion of the International Search Authority PCT/IB2014/064564 (WO 2015/044836).
International Search Report (ISR) PCT/IB2014/064564 (WO 2015/044836).
International Preliminary Report on Patentability (IPRP) PCT/US2006/060927 (WO 2007/059513).
Written Opinion of the International Search Authority PCT/US2006/060927 (WO 2007/059513).
International Search Report (ISR) PCT/US2006/060927 (WO 2007/059513).
European Search Report EP1948690 A1 (EP06846312.4).
Supplementary European Search Report EP1948690 A1 (EP06846312.4).
International Preliminary Report on Patentability (IPRP) PCT/US2012/058279 (WO 2013/049804).
Written Opinion of the International Search Authority PCT/US2012/058279 (WO 2013/049804).
International Search Report (ISR) PCT/US2012/058279 (WO 2013/049804).
"SEQ ID No. 2 mi file" uploaded as partial result from PTO search file entitled "Sequence Search—20070801_095501_pct-us06-60-20070801_095501_pct-us06-60927-2-.mi" in order to demonstrate homology of claimed sequence to previously published sequence (2007); (cited in International Search Report of PCT/US2006/60927).
Al-Tamimi et al., Coagulation-induced shedding of platelet glycoprotein VI mediated by factor Xa. Blood 117:3912-3920 (Sep. 18, 2011).
Bajaj and Birktoft, "Human Factor IX and Factor IXa", Methods Enzymol.; 222; pp. 96-128; 1993.
Bianchini, E.P., et al. "Mapping of the catalytic groove preferences of factor Xa reveals an inadequate selectivity for its macromolecule substrates." J Biol Chem. Jun. 7, 2002;277(23):20527-34. Epub Mar. 29, 2002.
Bock et al. "Isolation of human blood coagulation α-factor Xa by soybean-trypsin inhibitor-Sepharose chromatography and its active-site titration with fluorescein mono-p-guanidinobenzoate." Arch. Bioch. Biophys. 273; pp. 375-388; 1989.
Bode et al. "The refined 1.9 Å crystal structure of human alpha-thrombin: interaction with D-Phe-Pro-Arg chloromethylketone and significance of the Tyr-Pro-Trp insertion segment." EMBO J.; 8(11); pp. 3467-3475; 1989.
Brandsteller et al., "X-ray Structure of Active Site-inhibited Clotting Factor Xa."; J. Biol. Chem.; 271; pp. 29988-29992 1996.
Bunce, M. et al., "Zymogen-like factor Xa variants restore thrombin generation and effectively bypass the intrinsic pathway in vitro." Blood, Jan. 6, 2011; vol. 117, No. 1:290-298.
Bunce, Matthew W.; Toso, Raffaella; Arruda, Valder R.; Camire, Rodney M. Zymogen-Like Factor Xa Variants Restore Thrombin Generation and Effectively Bypass the Intrinsic Pathway in Vitro. Blood. 112(11). Nov. 16, 2008. Abstract from 2008 Annual Meeting of the American Society of Hematology.
Camire R.M., Bunce M., Ivanciu L., Toso R., Downey H., Liu J., Arruda V. Novel factor XA variants for improving hemostasis in hemophilia. Journal of Thrombosis and Haemostasis. 7 (S2) (pp. 96), Jul. 2009. Abstract from 22nd Congress of the International Society of Thrombosis and Haemostasis.
Camire R.M., Bunce M., Ivanciu L., Toso R., Downey H.D., Liu J.-H., Arruda V.R. The development of novel hemostatic bypassing molecules. Blood. 114(22). Nov. 20, 2009. Abstract from 2009 Annual Meeting of the American Society of Hematology.
Camire, R. M., Larson, P. J., Stafford, D. W., and High, K. A. (2000) Enhanced γ-carboxylation of recombinant factor X using a chimeric construct containing the prothrombin propeptide. Biochemistry 39, 14322-14329.
Camire, R. "Prothrombinase assembly and S1 site occupation restore the catalytic activity of FXa impaired by mutation at the

(56) References Cited

OTHER PUBLICATIONS sodium-binding site." Journal of Biological Chemistry, 277(40):37863-37870 (Oct. 4, 2002).
Chase, T. and Shaw, E. (1969) Comparison of the esterase activities of trypsin, plasmin, and thrombin on guanidinobenzoate esters. Titration of the enzymes. Biochemistry. 8, 2212-2224.
Dahlback, B. and Stenflo, J. (1978) Binding of bovine coagulation factor Xa to platelets. Biochemistry 17, 4938-4945.
Duckert, P., et al., Prediction of proprotein convertase cleavage sites, Protein Engineering, Design & Selection 17(1):107-112 (2004).
Eigenbrot, C., Kirchhofer, D., Dennis, M. S., Santell, L., Lazarus, R. A., Stamos, J., and Ultsch MH; The factor VII zymogen structure reveals reregistration of beta strands during activation. Structure 9, 627-636; 2001.
Friedrich, R., et al. "Staphylocoagulase is a prototype for the mechanism of cofactor-induced zymogen activation." Nature, 425: 535-539 (Oct. 2, 2003).
Furie, B. and Furie, B. C. (1976) Spectral changes in bovine factor X associated with activation by the venom coagulant protein Vipera russelli. J.Biol. Chem. 251, 6807-6814.
Guo, H.H., et al. "Protein tolerance to random amino acid change." Proc. Natl. Acad. Sci. USA.;101 (25):9205-10; Jun. 22, 2004.
Hedstrom, L., et al. "Hydrophobic interactions control zymogen activation in the trypsin family of serine proteases." Biochemistry, 35(14): 4515-4523 (1996).
Hertzberg, M, "Biochemistry of Factor X", Blood Reviews 8:56-62 (1994).
Holt, K., Human Coagulation Factor X, Swiss Prot accession No. Q5JVE7, direct submission May 2005.
Hult, K., et al. "Engineered enzymes for improved organic synthesis." Curr Opin Biotechnol. Aug. 2003;14(4):395-400.
Ion Exchange Chromatography & Chromatofocusing Principles and Methods Handbook published by GE Healthcare (2010).
Ivanciu L., Camire R.M. "Modulation of FXa zymogenicity yields variants that improve hemostasis in hemophilia." Journal of Thrombosis and Haemostasis. 11 (p. 270), Jul. 2013. Abstract from 24th Congress of the International Society on Thrombosis and Haemostasis.
Ivanciu L., Camire R.M. "Selective alteration of FXa zymogenicity provides a dynamic range of variants that improve hemostasis in hemophilia." Blood. 118(21). Nov. 18, 2011. Abstract from 2011 Annual Meeting of the American Society of Hematology.
Ivanciu L., et al., "A zymogen-like factor Xa variant corrects the coagulation defect in hemophilia." Nat. Biotechnol. 29:1028-33 (2011); and 11 pages supplemental figures and tables.
Ivanciu L., Toso R., Schlachterman A., Downey H., Liu J., Arruda V.R., Camire R.M. Zymogen-like factor Xa variants improve hemostasis in hemophilia mice. Journal of Thrombosis and Haemostasis. 7 (S2) (pp. 82-83), Jul. 2009. Abstract from 22nd Congress of the International Society of Thrombosis and Haemostasis.
Ivanciu, Lacramioara; Toso, Raffaella; Schlachterman, Alexander; Downey, Harre; Liu, Jain-Hua; Arruda, Valder R.; Camire, Rodney M.; "Factor Xa Variants as Novel Bypass Agents for the Treatment of Hemophilia in Murine Models." Blood. 112(11). Nov. 16, 2008. Abstract from 2008 Annual Meeting of the American Society of Hematology.
Jesty et al., The activation of coagulation factor X, J Biol Chem. Jun. 25, 1975;250(12):4497-504.
Kamal, AH, et al., How to interpret and pursue an abnormal prothrombin time, activated partial thromboplastin time, and bleeding time in adults, Mayo Clin Proc. 82(7):864-873 (2007).
Keyt, B., Furie, B. C., and Furie, B. (1982) Structural transitions in bovine factor X associated with metal binding and zymogen activation. Studies using conformational-specific antibodies. J. Biol. Chem. 257, 8687-8695.
Khan, A.R., et al. "Molecular mechanisms for the conversion of zymogens to active proteolytic enzymes." Protein Science. 1998;7(4):815-836.

Larson, P. J., Camire, R. M., Wong, D., Fasano, N. C., Monroe, D. M., Tracy, P. B., and High, K. A. (1998) Structure/function analyses of recombinant variants of human factor Xa: Factor Xa incorporation into prothrombinase on the activated platelet surface is not mimicked by synthetic phospholipid vesicles. Biochemistry 37, 5029-5038.
Madison, E., Kobe, A., Gething, M., Sambrook, J. F., and Goldsmith, E. (1993) Converting tissue plasminogen activator to a zymogen: A regulatory triad of Asp-His-Ser. Science 262, 419-421.
Madoiwa, S. et al., Autoantibody against prothrombin aberrantly alters the proenzyme to facilitate formation of a complex with its physiological inhibitor antithrombin III without thrombin conversion, Blood 97(12):3783-3789 (2001).
Maekawa H. et al., Molecular defect in factor IX Tokyo: substitution of valine-182 by alanine at position P2' in the second cleavage site by factor XIa resulting in impaired activation. Biochemistry, 32, 6146-6151 (1993).
Miletich, J.P., Jackson, C. M., and Majerus, P. W. (1978) Properties of the factor Xa binding site on human platelets. J. Biol.Chem. 253, 6908-6916.
Multimodal Chromatography Handbook published by GE Healthcare Life Sciences (2013).
Ngo, J.T., et al. "Computational Complexity, Protein Structure Prediction and the Levinthal Paradox." In the Protein Folding Problem and Tertiary Structure Prediction, K.M. Merz and S.M. Le Grand, eds., Birkháuser Boston (1994), pp. 492-495.
Persson, E., Hogg, P. J., and Stenflo, J. (1993) Effects of Ca2+ binding on the protease module of factor Xa and its interaction with factor Va: evidence for two Gla-independent Ca2+ binding sites in factor Xa. J Biol Chem 268, 22531-22539.
Persson, E., Valcarce, C., and Stenflo, J. (1991) The γ-carboxyglutamic acid and epidermal growth factor-like domains of factor X. Effect of isolated domains on prothrombin activation and endothelial cell binding of factor X. J Biol Chem 266, 2458.
Pittman D., Nichols T., Camire R., Toso R., Merricks E., Raymer R., De Friess N., Leary B., Parng C., Arkin S., Fruebis J. A factor Xa variant restores hemostasis in a hemophilia a dog model. Haemophilia. 18 (pp. 87-88), Jul. 2012. Absract from 30th International Congress of the World Federation of Hemophilia.
Raju, TS, et al., Species-specific variation in glycosylation of IgG: evidence for the species-specific sialylation and branch-specific galactosylation and importance for engineering recombinant glycoprotein therapeutics, Glycobiology 10(5):477-486 (2000).
Renatus, M., Engh, R A., Stubbs, M. T., Huber, R., Fischer, S., Kohnert, U., and Bode, W. (1997) Lysine 156 promotes the anomalous proenzyme activity of tPA: X-ray crystal structure of single-chain human tPA. EMBO J 16, 4797-4805.
Rezaie, A. R (2000) Identification of basic residues in the heparin-binding exosite of factor Xa critical for heparin and factor Va binding. J. Biol. Chem. 275, 3320-3327.
Rezaie, A. R. (1996) Role of residue 99 at the S2 subsite of factor Xa and activated protein C in enzyme specificity. J. Biol. Chem. 271, 23807-23814.
Rezaie, A. R. and Esmon, C. T. (1994) Asp-70 to Lys mutant of factor X lacks high affinity Ca2+ binding site yet retains function. J. Biol. Chem. 269, 21495-21499.
Bode, W., et al. The refined 1.9-A X-ray crystal structure of D-Phe-Pro-Arg chloromethylketone-inhibited human alpha-thrombin: structure analysis, overall structure, electrostatic properties, detailed active-site geometry, and structure-function relationships. Protein Sci. Apr. 1992;1(4):426-71.
Di Scipio, RG, et al. Activation of human factor X (Stuart factor) by a protease from Russell's Viper Venom. Biochem. 16(24):5253-5260 (1977).
Fujikawa, K, et al. Activation of bovine factor X (Stuart factor): Conversion of factor Xaalpha to factor Xabeta. PNAS 72(9):3359-3363 (1975).
Fung, MR, et al. Characterization of an almost full-length cDNA coding for human blood coagulation factor X. PNAS 82:3591-3595 (1985).
Hollenbach S et al: "Bolus administration of PRT064445, a recombinant Factor Xa inhibitor antidote, reverses blood loss and PD markers in a rat model following enoxaparin induced anticoagula-

(56) References Cited

OTHER PUBLICATIONS tion", European Heart Journal, vol. 33, no. Suppl, Jan. 1, 2012 (Jan. 1, 2012), pp. 309-310, XP009177324, Oxford University Press, GB ISSN: 0195-668X.
Kwan, E., et al. Self-activating factor X derivative fused to the C-terminus of a cellulose-binding module: Production and properties. Biotechnol Bioeng. Sep. 30, 2002;79(7):724-32.
Leytus, SP, et al. Characterization of a cDNA coding for human factor X. PNAS 81:3699-3702 (1984).
Louvain-Quintard, VB., et al, Thrombin-activable factor X re-establishes an intrinsic amplification in tenase-deficient plasmas. J Biol Chem. Dec. 16, 2005;280(50):41352-9. Epub Oct. 5, 2005.
Lu G et al: "Reconstructed recombinant factor Xa as an antidote to reverse anticoagulation by factor Xa inhibitors", Journal of Thrombosis and Haemostasis, vol. 7, no. suppl. 2, Jul. 1, 2009 (Jul. 1, 2009), pp. 309/OC-TH, XP009177312, Blackwell Publishing, Oxford, GB ISSN: 1538-7933.
Lu, G., et al. A specific antidote for reversal of anticoagulation by direct and indirect inhibitors of coagulation factor Xa. Nat Med. Apr. 2013;19(4):446-51. doi: 10.1038/nm.3102. Epub Mar. 3, 2013. Supplement, pp. 1-3.
Mertens, K and Bertina, RM. Pathways in the activation of human coagulation factor X. Biochem. J. 185:647-658 (1980).
Morris, HR, et al. Mass-spectrometric identification and sequence location of the ten residues of the new amino acid (gamma-carboxyglutamic acid) in the N-terminal region of prothrombin. Biochem. J. 153:663-679 (1976).
PCT/IB2015/050313 ISA Written Opinion.
Pittman D., Shields K., Rose-Miranda R., Losey H., Erbe D., Ivanciu L. A novel factor Xa variant for treatment of bleeding disorders. Haemophilia. 16 (pp. 44-45), Jul. 2010. Abstract from 29th International Congress of the World Federation of Hemophilia.
Pryzdial, Elg et al., Prothrombinase Components Can Accelerate Tissue Plasminogen Activator-catalyzed Plasminogen Activation. J. of Biological Chem., vol. 270, No. 30, pp. 17871-17877, 1995.
Pryzdial, Elg and Kessler, GE. Autoproteolysis or Plasmin-mediated Cleavage of Factor Xaa Exposes a Plasminogen Binding Site and Inhibits Coagulation., J. of Biological Chem., vol. 271, No. 28, pp. 16614-16620, 1996.
Pryzdial, Elg and Kessler, GE. Kinetics of Blood coagulation Factor Xaalpha Autoproteolytic Conversion to Factor Xabeta., J. of Biological Chem., vol. 271, No. 28, pp. 16621-16626, 1996.
Quade-Lyssy, P., et al. Engineered Factor VII, Factor IX, and Factor X Variants for HemophiliaGene Therapy. J Genet Syndr Gene Ther, 2012, pp. 1-7, XP002722748, ISSN: 2157-7412.
Rudolph, AE, et al. The role of the factor X activation peptide: a deletion mutagenesis approach. Thromb Haemost. Nov. 2002;88(5):756-62.
Seegers, WH and Ghosh, A. The Activation of Factor X and Factor XB with Factor VII or Protein M., Thrombosis Research, vol. 17, pp. 501-506, 1980.
Stenflo, J et al. Beta-Hydroxyasparagine in domains homologous to the epidermal growth factor precursor in vitamin K-dependent protein S., vol. 84, pp. 368-372, 1987.
Thalji, N.K. Reversal of Direct Factor Xa Inhibitors Using Factor Xa Zymogen-Like Variants. 28th Annual National MD/PhD Student Conference—Keystone, Colorado, Jul. 26-28, 2013.
Thalji N.K., Patel-Rett S., Jasuja R, Fruebis J., Pittman D., Camire R.M. Zymogen-like FXa is an effective pro-hemostatic to reverse the anticoagulant effects of direct FXa inhibitors. Blood. Conference: 55th Annual Meeting of the American Society of Hematology, ASH 2013 New Orleans, LA United States. Conference Publication: (var.pagings). 122 (21) (no pagination), 2013. Date of Publication: Oct. 21, 2013.

* cited by examiner

FIG. 1A

Amino acid sequence of FX Variant Protein (SEQ ID NO:1)

```
  1  ANSFLEEMKKGHLERECMEETCSYEEAREVFEDSDKTNEFWNKYKDGDQC        50
 51  ETSPCQNQGKCKDGLGEYTCTCLEGFEGKNCELFTRKLCSLDNGDCDQFC       100
101  HEEQNSVVCSCARGYTLADNGKACIPTGPYPCGKQTLERRKRRKRLVGGQ       150
151  ECKDGECPWQALLINEENEGFCGGTILSEFYILTAAHCLYQAKRFKVRVG       200
201  DRNTEQEEGGEAVHEVEVVIKHNRFTKETYDFDIAVLRLKTPITFRMNVA       250
251  PACLPERDWAESTLMTQKTGIVSGFGRTHEKGRQSTRLKMLEVPYVDRNS       300
301  CKLSSSFIITQNMFCAGYDTKQEDACQGDSGGPHVTRFKDTYFVTGIVSW       350
351  GEGCARKGKYGIYTKVTAFLKWIDRSMKTRGLPKAKSHAPEVITSSPLK        399
```

FIG. 1B

Predicted amino acid sequence of FXa variant protein light chain (SEQ ID NO:2)

Predicted amino acid sequence of FXa variant protein heavy chain (SEQ ID NO:3)

```
001 L V G G Q E C K D G E C P W Q A L L I N E E N E G F C G G T 030
031 I L S E F Y I L T A A H C L Y Q A K R F K V R V G D R N T E 060
061 Q E E G G E A V H E V E V V I K H N R F T K E T Y D F D I A 090
091 V L R L K T P I T F R M N V A P A C L P E R D W A E S T L M 120
121 T Q K T G I V S G F G R T H E K G R Q S T R L K M L E V P Y 150
151 V D R N S C K L S S S F I I T Q N M F C A G Y D T K Q E D A 180
181 C Q G D S G G P H V T R F K D T Y F V T G I V S W G E G C A 210
211 R K G K Y G I Y T K V T A F L K W I D R S M K T R G L P K A 240
241 K S H A P E V I T S S P L K                               254
```

FIG. 1D cDNA encoding FX variant protein (SEQ ID NO:4)

```
ATGGGCGACGTCCGAGGCTTGCAGCTGCCTGGCCTGCCCTGGTGTAGCCTTG
TGCACAGCCAGCATGTGTTCCTGGCTCCTCAGCAAGCACGTCGCTGCTCCAGCGGGTCCGGCG
AGCCAATTCCTTTCTTGAAGAGATGAAGAAGACACCTCGAAAGAGAGTGCATGGAAGAGACC
TGCTCATACGAAGAGGCCCGCGAGGTCTTTGAGGACACAGCAGACGAAGAGAATGAATTCTGGAATA
AATACAAAGATGGCGACCAGTGTGAGACCAGTCCTTGCCAGAACCAGGGCAAATGTAAAGACGG
CCTCGGGGAATACACCTGCACCTGTTTAGAAGGATTCGAAGGAAAAACTGTGAATTATTCACA
CGGAAGCTCTGCAGCCTGGACAACGGGACTGTGACCAGTTCTGCCACGAGGAACAGAACTCTG
TGGTGTGCTCCTGCGCCCGCGGGTACACCCTGGCTGACAACGGCAAGGCCTGCATTCCCACAGG
GCCCTACCCCTGTGGGAAACAGACCCTGGAACGCAGGAAGAGGCGTAAGCGTCTCGTGGGAGGC
CAGGAATGCAAGGACGGGGAGTGTCCCTGGCAGGCCCTGCTCATCAATGAGGAAAACGAGGGTT
TCTGTGGTGGAACTATTCTGAGCGAGTTCTACATCCTAACGGCAGCCCACTGTCTCTACCAAGC
CAAGAGATTCAAGGTGAGGGTGGGTCATCAAGCACACAACCGGTTCACAAAGGAGACCTATGACTTCGACATCG
CACGAGGTGGAGGTGCTCAAGACCCCATCACCTTCCGCATGAAGGTGGCGCCTGCCTGCCTCCCCGA
CCGTGCTCGGCTGGGCCGAGTCCACGCTGATGACGCAGGCTCCAGGGATTGTGAGCGGCTTCGGGCGC
GCGTGACTGGGCCGAGTCCACGCTGATGACGCAGGCTCCAGGGATTGTGAGCGGCTTCGGGCGC
ACCAGAGAAGGGCCGGCAGTCCAGCAGCTTCATCATCCAGAACATGTTCTGTGCCGGCTACGACGCA
ACAGCTGCAAGCTGTCCAGCAGCTTCATCATCCAGAACATGTTCTGTGCCGGCTACGACACAC
CAAGCAGGAGGATGCCTGCCAGGGGGACAGCGGGGCCCGCACGTCACCCGCTTCACCCGACACC
TACTTCGTGACAGGCATCGTCAGCTGGGGAGAGGGCTGTGCCCGTAAGGGAAGTACGGGATCT
ACACCAAGGTCACCGCCTTCCTCAAGTGGATCGACAGGTCCATGAAAACCAGGGCTTGCCCAA
GGCCAAGAGCCATGCCCCGGAGGTCATAAACGTCCTCTCCATTAAAGTGA
```

Light Chain

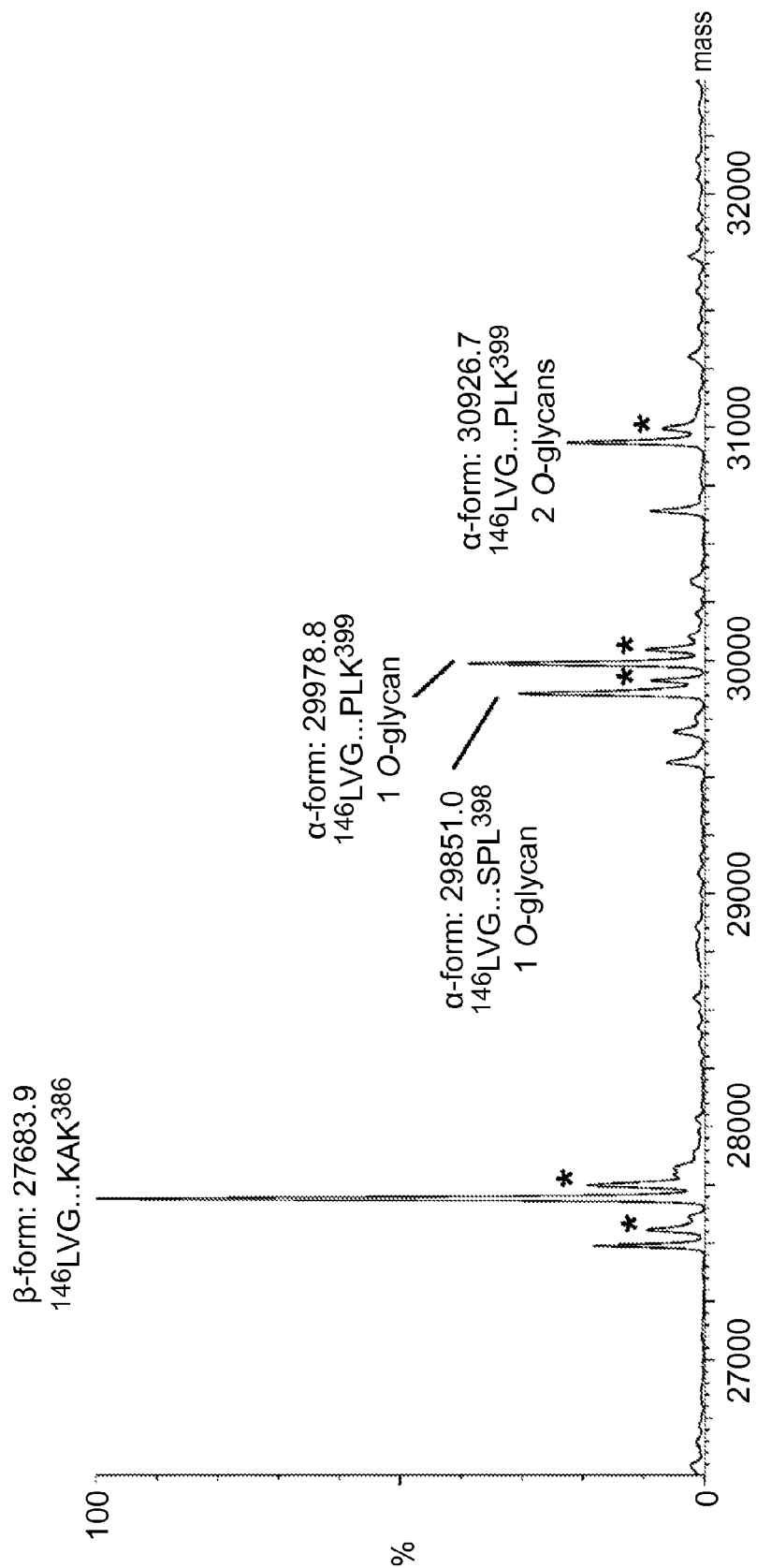

SEQUENCE LISTING

```
<160> NUMBER OF SEQ ID NOS: 46

<210> SEQ ID NO 1
<211> LENGTH: 399
<212> TYPE: PRT
<213> ORGANISM: Artificial Sequence
<220> FEATURE:
<223> OTHER INFORMATION: Modified human protein sequence

<400> SEQUENCE: 1

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Arg Lys
    130                 135                 140

Arg Leu Val Gly Gly Gln Glu Cys Lys Asp Gly Glu Cys Pro Trp Gln
145                 150                 155                 160

Ala Leu Leu Ile Asn Glu Glu Asn Glu Gly Phe Cys Gly Gly Thr Ile
                165                 170                 175

Leu Ser Glu Phe Tyr Ile Leu Thr Ala Ala His Cys Leu Tyr Gln Ala
            180                 185                 190

Lys Arg Phe Lys Val Arg Val Gly Asp Arg Asn Thr Glu Gln Glu Glu
        195                 200                 205
```

Gly Gly Glu Ala Val His Glu Val Val Ile Lys His Asn Arg
    210             215                 220

Phe Thr Lys Glu Thr Tyr Asp Phe Asp Ile Ala Val Leu Arg Leu Lys
225                 230                 235                 240

Thr Pro Ile Thr Phe Arg Met Asn Val Ala Pro Ala Cys Leu Pro Glu
                245                 250                 255

Arg Asp Trp Ala Glu Ser Thr Leu Met Thr Gln Lys Thr Gly Ile Val
            260                 265                 270

Ser Gly Phe Gly Arg Thr His Glu Lys Gly Arg Gln Ser Thr Arg Leu
        275                 280                 285

Lys Met Leu Glu Val Pro Tyr Val Asp Arg Asn Ser Cys Lys Leu Ser
290                 295                 300

Ser Ser Phe Ile Ile Thr Gln Asn Met Phe Cys Ala Gly Tyr Asp Thr
305                 310                 315                 320

Lys Gln Glu Asp Ala Cys Gln Gly Asp Ser Gly Gly Pro His Val Thr
                325                 330                 335

Arg Phe Lys Asp Thr Tyr Phe Val Thr Gly Ile Val Ser Trp Gly Glu
            340                 345                 350

Gly Cys Ala Arg Lys Gly Lys Tyr Gly Ile Tyr Thr Lys Val Thr Ala
        355                 360                 365

Phe Leu Lys Trp Ile Asp Arg Ser Met Lys Thr Arg Gly Leu Pro Lys
370                 375                 380

Ala Lys Ser His Ala Pro Glu Val Ile Thr Ser Ser Pro Leu Lys
385                 390                 395

<210> SEQ ID NO 2
<211> LENGTH: 145
<212> TYPE: PRT
<213> ORGANISM: Artificial Sequence
<220> FEATURE:
<223> OTHER INFORMATION: Modified human protein sequence

<400> SEQUENCE: 2

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Arg Lys
    130                 135                 140

Arg
145

<210> SEQ ID NO 3

<211> LENGTH: 254
<212> TYPE: PRT
<213> ORGANISM: Artificial Sequence
<220> FEATURE:
<223> OTHER INFORMATION: Modified human protein sequence

<400> SEQUENCE: 3

```
Leu Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ser Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250
```

<210> SEQ ID NO 4
<211> LENGTH: 1329
<212> TYPE: DNA
<213> ORGANISM: Artificial Sequence
<220> FEATURE:
<223> OTHER INFORMATION: Modified human DNA sequence

<400> SEQUENCE: 4

```
atggcgcacg tccgaggctt gcagctgcct ggctgcctgg ccctggctgc cctgtgtagc      60
cttgtgcaca gccagcatgt gttcctggct cctcagcaag cacggtcgct gctccagcgg     120
gtccggcgag ccaattcctt tcttgaagag atgaagaaag acacctcga agagagtgc      180 atggaagaga cctgctcata cgaagaggcc cgcgaggtct ttaggacag cgacaagacg     240 aatgaattct ggaataaata caaagatggc gaccagtgtg agaccagtcc ttgccagaac     300
cagggcaaat gtaagacgg cctcggggaa tacacctgca cctgtttaga aggattcgaa     360
ggcaaaaact gtgaattatt cacacggaag ctctgcagcc tggacaacgg ggactgtgac     420
```

```
cagttctgcc acgaggaaca gaactctgtg gtgtgctcct gcgcccgcgg gtacaccctg    480
gctgacaacg gcaaggcctg cattcccaca gggccctacc cctgtgggaa acagaccctg    540
gaacgcagga agaggcgtaa gcgtctcgtg ggaggccagg aatgcaagga cggggagtgt    600
ccctggcagg ccctgctcat caatgaggaa aacgagggtt tctgtggtgg aactattctg    660
agcgagttct acatcctaac ggcagcccac tgtctctacc aagccaagag attcaaggtg    720
agggtaggtg accggaacac ggagcaggag gagggcggtg aggcggtgca cgaggtggag    780
gtggtcatca agcacaaccg gttcacaaag gagacctatg acttcgacat cgccgtgctc    840
cggctcaaga ccccatcac cttccgcatg aacgtggcgc ctgcctgcct ccccgagcgt    900
gactgggccg agtccacgct gatgacgcag aagacgggga ttgtgagcgg cttcgggcgc    960
acccacgaga agggccggca gtccaccagg ctcaagatgc tggaggtgcc ctacgtggac   1020
cgcaacagct gcaagctgtc cagcagcttc atcatcaccc agaacatgtt ctgtgccggc   1080
tacgacacca gcaggagga tgcctgccag ggggacagcg ggggcccgca cgtcacccgc   1140
ttcaaggaca cctacttcgt gacaggcatc gtcagctggg gagagggctg tgcccgtaag   1200
gggaagtacg gatctacac caaggtcacc gccttcctca gtggatcga caggtccatg   1260 aaaaccaggg gcttgcccaa ggccaagagc catgccccgg aggtcataac gtcctctcca   1320
ttaaagtga                                                            1329
```

<210> SEQ ID NO 5  
<211> LENGTH: 6  
<212> TYPE: PRT  
<213> ORGANISM: Artificial Sequence  
<220> FEATURE:  
<223> OTHER INFORMATION: PACE site

<400> SEQUENCE: 5

Arg Lys Arg Arg Lys Arg  
1               5

<210> SEQ ID NO 6  
<211> LENGTH: 139  
<212> TYPE: PRT  
<213> ORGANISM: Artificial Sequence  
<220> FEATURE:  
<223> OTHER INFORMATION: Modified human protein sequence

<400> SEQUENCE: 6

Ala Asn Ser Phe Leu Glu Glu Met Lys Lys Gly His Leu Glu Arg Glu  
1               5                   10                  15

Cys Met Glu Glu Thr Cys Ser Tyr Glu Glu Ala Arg Glu Val Phe Glu  
            20                  25                  30

Asp Ser Asp Lys Thr Asn Glu Phe Trp Asn Lys Tyr Lys Asp Gly Asp  
        35                  40                  45

Gln Cys Glu Thr Ser Pro Cys Gln Asn Gln Gly Lys Cys Lys Asp Gly  
    50                  55                  60

Leu Gly Glu Tyr Thr Cys Thr Cys Leu Glu Gly Phe Glu Gly Lys Asn  
65                  70                  75                  80

Cys Glu Leu Phe Thr Arg Lys Leu Cys Ser Leu Asp Asn Gly Asp Cys  
                85                  90                  95

Asp Gln Phe Cys His Glu Glu Gln Asn Ser Val Val Cys Ser Cys Ala  
            100                 105                 110

Arg Gly Tyr Thr Leu Ala Asp Asn Gly Lys Ala Cys Ile Pro Thr Gly  
        115                 120                 125

Pro Tyr Pro Cys Gly Lys Gln Thr Leu Glu Arg
    130                 135

<210> SEQ ID NO 7
<211> LENGTH: 140
<212> TYPE: PRT
<213> ORGANISM: Artificial Sequence
<220> FEATURE:
<223> OTHER INFORMATION: Modified human protein sequence

<400> SEQUENCE: 7

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg
    130                 135                 140

<210> SEQ ID NO 8
<211> LENGTH: 5
<212> TYPE: PRT
<213> ORGANISM: Artificial Sequence
<220> FEATURE:
<223> OTHER INFORMATION: Proteolytic fragment

<400> SEQUENCE: 8

Lys Arg Arg Lys Arg
1               5

<210> SEQ ID NO 9
<211> LENGTH: 141
<212> TYPE: PRT
<213> ORGANISM: Artificial Sequence
<220> FEATURE:
<223> OTHER INFORMATION: Modified human protein sequence

<400> SEQUENCE: 9

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

```
Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Lys
130                 135                 140

<210> SEQ ID NO 10
<211> LENGTH: 4
<212> TYPE: PRT
<213> ORGANISM: Artificial Sequence
<220> FEATURE:
<223> OTHER INFORMATION: Proteolytic fragment

<400> SEQUENCE: 10

Arg Arg Lys Arg
1

<210> SEQ ID NO 11
<211> LENGTH: 142
<212> TYPE: PRT
<213> ORGANISM: Artificial Sequence
<220> FEATURE:
<223> OTHER INFORMATION: Modified human protein sequence

<400> SEQUENCE: 11

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Lys Arg
        130                 135                 140

<210> SEQ ID NO 12
<211> LENGTH: 143
<212> TYPE: PRT
<213> ORGANISM: Artificial Sequence
<220> FEATURE:
<223> OTHER INFORMATION: Modified human protein sequence

<400> SEQUENCE: 12

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
```

```
                35                  40                  45
Gln Cys Glu Thr Ser Pro Cys Gln Asn Gln Gly Lys Cys Lys Asp Gly
         50                  55                  60
Leu Gly Glu Tyr Thr Cys Thr Cys Leu Glu Gly Phe Glu Gly Lys Asn
 65                  70                  75                  80
Cys Glu Leu Phe Thr Arg Lys Leu Cys Ser Leu Asp Asn Gly Asp Cys
                 85                  90                  95
Asp Gln Phe Cys His Glu Glu Asn Ser Val Val Cys Ser Cys Ala
                100                 105                 110
Arg Gly Tyr Thr Leu Ala Asp Asn Gly Lys Ala Cys Ile Pro Thr Gly
            115                 120                 125
Pro Tyr Pro Cys Gly Lys Gln Thr Leu Glu Arg Arg Lys Arg Arg
       130                 135                 140

<210> SEQ ID NO 13
<211> LENGTH: 144
<212> TYPE: PRT
<213> ORGANISM: Artificial Sequence
<220> FEATURE:
<223> OTHER INFORMATION: Modified human protein sequence

<400> SEQUENCE: 13

Ala Asn Ser Phe Leu Glu Glu Met Lys Lys Gly His Leu Glu Arg Glu
 1               5                  10                  15
Cys Met Glu Glu Thr Cys Ser Tyr Glu Ala Arg Glu Val Phe Glu
                 20                  25                  30
Asp Ser Asp Lys Thr Asn Glu Phe Trp Asn Lys Tyr Lys Asp Gly Asp
             35                  40                  45
Gln Cys Glu Thr Ser Pro Cys Gln Asn Gln Gly Lys Cys Lys Asp Gly
         50                  55                  60
Leu Gly Glu Tyr Thr Cys Thr Cys Leu Glu Gly Phe Glu Gly Lys Asn
 65                  70                  75                  80
Cys Glu Leu Phe Thr Arg Lys Leu Cys Ser Leu Asp Asn Gly Asp Cys
                 85                  90                  95
Asp Gln Phe Cys His Glu Glu Gln Asn Ser Val Val Cys Ser Cys Ala
                100                 105                 110
Arg Gly Tyr Thr Leu Ala Asp Asn Gly Lys Ala Cys Ile Pro Thr Gly
            115                 120                 125
Pro Tyr Pro Cys Gly Lys Gln Thr Leu Glu Arg Arg Lys Arg Arg Lys
       130                 135                 140

<210> SEQ ID NO 14
<211> LENGTH: 253
<212> TYPE: PRT
<213> ORGANISM: Artificial Sequence
<220> FEATURE:
<223> OTHER INFORMATION: Modified human protein sequence

<400> SEQUENCE: 14

Leu Val Gly Gly Gln Glu Cys Lys Asp Gly Glu Cys Pro Trp Gln Ala
 1               5                  10                  15
Leu Leu Ile Asn Glu Glu Asn Glu Gly Phe Cys Gly Gly Thr Ile Leu
                 20                  25                  30
Ser Glu Phe Tyr Ile Leu Thr Ala Ala His Cys Leu Tyr Gln Ala Lys
             35                  40                  45
Arg Phe Lys Val Arg Val Gly Asp Arg Asn Thr Glu Gln Glu Glu Gly
         50                  55                  60
```

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
            85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ser Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu
                245                 250

<210> SEQ ID NO 15
<211> LENGTH: 10
<212> TYPE: PRT
<213> ORGANISM: Artificial Sequence
<220> FEATURE:
<223> OTHER INFORMATION: Peptide fragment
<220> FEATURE:
<221> NAME/KEY: misc_feature
<222> LOCATION: (6)..(7)
<223> OTHER INFORMATION: Xaa can be any naturally occurring amino acid

<400> SEQUENCE: 15

Ala Asn Ser Phe Leu Xaa Xaa Met Lys Lys
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Peptide fragment
<220> FEATURE:
<221> NAME/KEY: misc_feature
<222> LOCATION: (7)..(7)
<223> OTHER INFORMATION: Xaa can be any naturally occurring amino acid

<400> SEQUENCE: 16

Leu Val Gly Gly Gln Glu Xaa Lys Asp Gly
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Peptide fragment

<400> SEQUENCE: 17

```
Ala Asn Ser Phe Leu Glu Glu Met Lys
1               5

<210> SEQ ID NO 18
<211> LENGTH: 26
<212> TYPE: PRT
<213> ORGANISM: Artificial Sequence
<220> FEATURE:
<223> OTHER INFORMATION: Peptide fragment

<400> SEQUENCE: 18

Gly His Leu Glu Arg Glu Cys Met Glu Glu Thr Cys Ser Tyr Glu Glu
1               5                   10                  15

Ala Arg Glu Val Phe Glu Asp Ser Asp Lys
            20                  25

<210> SEQ ID NO 19
<211> LENGTH: 7
<212> TYPE: PRT
<213> ORGANISM: Artificial Sequence
<220> FEATURE:
<223> OTHER INFORMATION: Peptide fragment

<400> SEQUENCE: 19

Thr Asn Glu Phe Trp Asn Lys
1               5

<210> SEQ ID NO 20
<211> LENGTH: 15
<212> TYPE: PRT
<213> ORGANISM: Artificial Sequence
<220> FEATURE:
<223> OTHER INFORMATION: Peptide fragment

<400> SEQUENCE: 20

Asp Gly Asp Gln Cys Glu Thr Ser Pro Cys Gln Asn Gln Gly Lys
1               5                   10                  15

<210> SEQ ID NO 21
<211> LENGTH: 17
<212> TYPE: PRT
<213> ORGANISM: Artificial Sequence
<220> FEATURE:
<223> OTHER INFORMATION: Peptide fragment

<400> SEQUENCE: 21

Asp Gly Leu Gly Glu Tyr Thr Cys Thr Cys Leu Glu Gly Phe Glu Gly
1               5                   10                  15

Lys

<210> SEQ ID NO 22
<211> LENGTH: 8
<212> TYPE: PRT
<213> ORGANISM: Artificial Sequence
<220> FEATURE:
<223> OTHER INFORMATION: Peptide fragment

<400> SEQUENCE: 22

Asn Cys Glu Leu Phe Thr Arg Lys
1               5

<210> SEQ ID NO 23
<211> LENGTH: 35
<212> TYPE: PRT
<213> ORGANISM: Artificial Sequence
```

<220> FEATURE:
<223> OTHER INFORMATION: Peptide fragment

<400> SEQUENCE: 23

Leu Cys Ser Leu Asp Asn Gly Asp Cys Asp Gln Phe Cys His Glu Glu
1               5                   10                  15

Gln Asn Ser Val Val Cys Ser Cys Ala Arg Gly Tyr Thr Leu Ala Asp
            20                  25                  30

Asn Gly Lys
        35

<210> SEQ ID NO 24
<211> LENGTH: 12
<212> TYPE: PRT
<213> ORGANISM: Artificial Sequence
<220> FEATURE:
<223> OTHER INFORMATION: Peptide fragment

<400> SEQUENCE: 24

Ala Cys Ile Pro Thr Gly Pro Tyr Pro Cys Gly Lys
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Peptide fragment

<400> SEQUENCE: 25

Gln Thr Leu Glu Arg Arg Lys
1               5

<210> SEQ ID NO 26
<211> LENGTH: 6
<212> TYPE: PRT
<213> ORGANISM: Artificial Sequence
<220> FEATURE:
<223> OTHER INFORMATION: Peptide fragment

<400> SEQUENCE: 26

Gln Thr Leu Glu Arg Arg
1               5

<210> SEQ ID NO 27
<211> LENGTH: 5
<212> TYPE: PRT
<213> ORGANISM: Artificial Sequence
<220> FEATURE:
<223> OTHER INFORMATION: Peptide fragment

<400> SEQUENCE: 27

Gln Thr Leu Glu Arg
1               5

<210> SEQ ID NO 28
<211> LENGTH: 8
<212> TYPE: PRT
<213> ORGANISM: Artificial Sequence
<220> FEATURE:
<223> OTHER INFORMATION: Peptide fragment

<400> SEQUENCE: 28

Leu Val Gly Gly Gln Glu Cys Lys
1               5

<210> SEQ ID NO 29
<211> LENGTH: 40
<212> TYPE: PRT
<213> ORGANISM: Artificial Sequence
<220> FEATURE:
<223> OTHER INFORMATION: Peptide fragment

<400> SEQUENCE: 29

Asp Gly Glu Cys Pro Trp Gln Ala Leu Leu Ile Asn Glu Glu Asn Glu
1               5                   10                  15

Gly Phe Cys Gly Gly Thr Ile Leu Ser Glu Phe Tyr Ile Leu Thr Ala
                20                  25                  30

Ala His Cys Leu Tyr Gln Ala Lys
            35                  40

<210> SEQ ID NO 30
<211> LENGTH: 25
<212> TYPE: PRT
<213> ORGANISM: Artificial Sequence
<220> FEATURE:
<223> OTHER INFORMATION: Peptide fragment

<400> SEQUENCE: 30

Val Arg Val Gly Asp Arg Asn Thr Glu Gln Glu Glu Gly Gly Glu Ala
1               5                   10                  15

Val His Glu Val Glu Val Val Ile Lys
            20                  25

<210> SEQ ID NO 31
<211> LENGTH: 6
<212> TYPE: PRT
<213> ORGANISM: Artificial Sequence
<220> FEATURE:
<223> OTHER INFORMATION: Peptide fragment

<400> SEQUENCE: 31

His Asn Arg Phe Thr Lys
1               5

<210> SEQ ID NO 32
<211> LENGTH: 13
<212> TYPE: PRT
<213> ORGANISM: Artificial Sequence
<220> FEATURE:
<223> OTHER INFORMATION: Peptide fragment

<400> SEQUENCE: 32

Glu Thr Tyr Asp Phe Asp Ile Ala Val Leu Arg Leu Lys
1               5                   10

<210> SEQ ID NO 33
<211> LENGTH: 28
<212> TYPE: PRT
<213> ORGANISM: Artificial Sequence
<220> FEATURE:
<223> OTHER INFORMATION: Peptide fragment

<400> SEQUENCE: 33

Thr Pro Ile Thr Phe Arg Met Asn Val Ala Pro Ala Cys Leu Pro Glu
1               5                   10                  15

Arg Asp Trp Ala Glu Ser Thr Leu Met Thr Gln Lys
                20                  25

<210> SEQ ID NO 34

```
<211> LENGTH: 13
<212> TYPE: PRT
<213> ORGANISM: Artificial Sequence
<220> FEATURE:
<223> OTHER INFORMATION: Peptide fragment

<400> SEQUENCE: 34

Thr Gly Ile Val Ser Gly Phe Gly Arg Thr His Glu Lys
1               5                   10

<210> SEQ ID NO 35
<211> LENGTH: 8
<212> TYPE: PRT
<213> ORGANISM: Artificial Sequence
<220> FEATURE:
<223> OTHER INFORMATION: Peptide fragment

<400> SEQUENCE: 35

Gly Arg Gln Ser Thr Arg Leu Lys
1               5

<210> SEQ ID NO 36
<211> LENGTH: 13
<212> TYPE: PRT
<213> ORGANISM: Artificial Sequence
<220> FEATURE:
<223> OTHER INFORMATION: Peptide fragment

<400> SEQUENCE: 36

Met Leu Glu Val Pro Tyr Val Asp Arg Asn Ser Cys Lys
1               5                   10

<210> SEQ ID NO 37
<211> LENGTH: 19
<212> TYPE: PRT
<213> ORGANISM: Artificial Sequence
<220> FEATURE:
<223> OTHER INFORMATION: Peptide fragment

<400> SEQUENCE: 37

Leu Ser Ser Ser Phe Ile Ile Thr Gln Asn Met Phe Cys Ala Gly Tyr
1               5                   10                  15

Asp Thr Lys

<210> SEQ ID NO 38
<211> LENGTH: 18
<212> TYPE: PRT
<213> ORGANISM: Artificial Sequence
<220> FEATURE:
<223> OTHER INFORMATION: Peptide fragment

<400> SEQUENCE: 38

Gln Glu Asp Ala Cys Gln Gly Asp Ser Gly Gly Pro His Val Thr Arg
1               5                   10                  15

Phe Lys

<210> SEQ ID NO 39
<211> LENGTH: 18
<212> TYPE: PRT
<213> ORGANISM: Artificial Sequence
<220> FEATURE:
<223> OTHER INFORMATION: Peptide fragment

<400> SEQUENCE: 39

Asp Thr Tyr Phe Val Thr Gly Ile Val Ser Trp Gly Glu Gly Cys Ala
1               5                   10                  15
```

Arg Lys

<210> SEQ ID NO 40
<211> LENGTH: 6
<212> TYPE: PRT
<213> ORGANISM: Artificial Sequence
<220> FEATURE:
<223> OTHER INFORMATION: Peptide fragment

<400> SEQUENCE: 40

Tyr Gly Ile Tyr Thr Lys
1               5

<210> SEQ ID NO 41
<211> LENGTH: 6
<212> TYPE: PRT
<213> ORGANISM: Artificial Sequence
<220> FEATURE:
<223> OTHER INFORMATION: Peptide fragment

<400> SEQUENCE: 41

Val Thr Ala Phe Leu Lys
1               5

<210> SEQ ID NO 42
<211> LENGTH: 7
<212> TYPE: PRT
<213> ORGANISM: Artificial Sequence
<220> FEATURE:
<223> OTHER INFORMATION: Peptide fragment

<400> SEQUENCE: 42

Trp Ile Asp Arg Ser Met Lys
1               5

<210> SEQ ID NO 43
<211> LENGTH: 6
<212> TYPE: PRT
<213> ORGANISM: Artificial Sequence
<220> FEATURE:
<223> OTHER INFORMATION: Peptide fragment

<400> SEQUENCE: 43

Thr Arg Gly Leu Pro Lys
1               5

<210> SEQ ID NO 44
<211> LENGTH: 13
<212> TYPE: PRT
<213> ORGANISM: Artificial Sequence
<220> FEATURE:
<223> OTHER INFORMATION: Peptide fragment

<400> SEQUENCE: 44

Ser His Ala Pro Glu Val Ile Thr Ser Ser Pro Leu Lys
1               5                   10

<210> SEQ ID NO 45
<211> LENGTH: 239
<212> TYPE: PRT
<213> ORGANISM: Artificial Sequence
<220> FEATURE:
<223> OTHER INFORMATION: Modified human protein sequence

<400> SEQUENCE: 45

Leu Val Gly Gly Gln Glu Cys Lys Asp Gly Glu Cys Pro Trp Gln Ala

```
            1               5                  10                 15
Leu Leu Ile Asn Glu Glu Asn Glu Gly Phe Cys Gly Gly Thr Ile Leu
                20                  25                 30

Ser Glu Phe Tyr Ile Leu Thr Ala Ala His Cys Leu Tyr Gln Ala Lys
                35                  40                 45

Arg Phe Lys Val Arg Val Gly Asp Arg Asn Thr Glu Gln Glu Glu Gly
                50                  55                 60

Gly Glu Ala Val His Glu Val Glu Val Val Ile Lys His Asn Arg Phe
65                  70                  75                 80

Thr Lys Glu Thr Tyr Asp Phe Asp Ile Ala Val Leu Arg Leu Lys Thr
                85                  90                 95

Pro Ile Thr Phe Arg Met Asn Val Ala Pro Ala Cys Leu Pro Glu Arg
                100                 105                110

Asp Trp Ala Glu Ser Thr Leu Met Thr Gln Lys Thr Gly Ile Val Ser
                115                 120                125

Gly Phe Gly Arg Thr His Glu Lys Gly Arg Gln Ser Thr Arg Leu Lys
                130                 135                140

Met Leu Glu Val Pro Tyr Val Asp Arg Asn Ser Cys Lys Leu Ser Ser
145                 150                 155                160

Ser Phe Ile Ile Thr Gln Asn Met Phe Cys Ala Gly Tyr Asp Thr Lys
                165                 170                175

Gln Glu Asp Ala Cys Gln Gly Asp Ser Gly Gly Pro His Val Thr Arg
                180                 185                190

Phe Lys Asp Thr Tyr Phe Val Thr Gly Ile Val Ser Trp Gly Glu Gly
                195                 200                205

Cys Ala Arg Lys Gly Lys Tyr Gly Ile Tyr Thr Lys Val Thr Ala Phe
                210                 215                220

Leu Lys Trp Ile Asp Arg Ser Met Lys Thr Arg Gly Leu Pro Lys
225                 230                 235

<210> SEQ ID NO 46
<211> LENGTH: 241
<212> TYPE: PRT
<213> ORGANISM: Artificial Sequence
<220> FEATURE:
<223> OTHER INFORMATION: Modified human protein sequence

<400> SEQUENCE: 46

Leu Val Gly Gly Gln Glu Cys Lys Asp Gly Glu Cys Pro Trp Gln Ala
1               5                   10                 15

Leu Leu Ile Asn Glu Glu Asn Glu Gly Phe Cys Gly Gly Thr Ile Leu
                20                  25                 30

Ser Glu Phe Tyr Ile Leu Thr Ala Ala His Cys Leu Tyr Gln Ala Lys
                35                  40                 45

Arg Phe Lys Val Arg Val Gly Asp Arg Asn Thr Glu Gln Glu Glu Gly
                50                  55                 60

Gly Glu Ala Val His Glu Val Glu Val Val Ile Lys His Asn Arg Phe
65                  70                  75                 80

Thr Lys Glu Thr Tyr Asp Phe Asp Ile Ala Val Leu Arg Leu Lys Thr
                85                  90                 95

Pro Ile Thr Phe Arg Met Asn Val Ala Pro Ala Cys Leu Pro Glu Arg
                100                 105                110

Asp Trp Ala Glu Ser Thr Leu Met Thr Gln Lys Thr Gly Ile Val Ser
                115                 120                125

Gly Phe Gly Arg Thr His Glu Lys Gly Arg Gln Ser Thr Arg Leu Lys
```

```
                    130                      135                      140
Met Leu Glu Val Pro Tyr Val Asp Arg Asn Ser Cys Lys Leu Ser Ser
145                      150                      155                      160

Ser Phe Ile Ile Thr Gln Asn Met Phe Cys Ala Gly Tyr Asp Thr Lys
                    165                      170                      175

Gln Glu Asp Ala Cys Gln Gly Asp Ser Gly Gly Pro His Val Thr Arg
                    180                      185                      190

Phe Lys Asp Thr Tyr Phe Val Thr Gly Ile Val Ser Trp Gly Glu Gly
                    195                      200                      205

Cys Ala Arg Lys Gly Lys Tyr Gly Ile Tyr Thr Lys Val Thr Ala Phe
                    210                      215                      220

Leu Lys Trp Ile Asp Arg Ser Met Lys Thr Arg Gly Leu Pro Lys Ala
225                      230                      235                      240

Lys
```

FXA VARIANT COMPOSITIONS

CROSS-REFERENCE TO RELATED APPLICATION

This application claims the benefit of U.S. Provisional Application No. 61/881,834, filed Sep. 24, 2013. This application is a continuation of International Patent Application PCT/IB2014/064564, filed Sep. 16, 2014, which claims the benefit of U.S. Provisional Application No. 61/881,834, filed Sep. 24, 2013. The disclosures of U.S. Provisional Application No. 61/881,834 and International Patent Application PCT/IB2014/064564 are incorporated herein by reference.

REFERENCE TO SEQUENCE LISTING

The Sequence Listing submitted concurrently herewith under 37 CFR §1.821 in a computer readable form (CRF) via EFS-Web as file name PC72049A_SEQLIST_ST25.txt is incorporated herein by reference. The electronic copy of the Sequence Listing was created on 24 Sep. 2014, with a file size of 31 kilobytes.

BACKGROUND OF THE INVENTION

Effective therapies are needed to control excessive bleeding in a range of clinical conditions where bleeding cannot be adequately controlled by medical or surgical intervention. This unmet need is particularly critical among patients with hemophilia, especially those in whom factor replacement therapy is rendered less efficacious due to the production of inhibitor antibodies.

Activated clotting Factor X (FXa) occupies a central position in the coagulation cascade at the convergence of the intrinsic and extrinsic coagulation pathways. Membrane-bound FXa, in the presence of its cofactor Factor Va (FVa), converts prothrombin to thrombin, which activates platelets and converts fibrinogen to fibrin to form the thrombus. In principle, replacement therapy with direct FXa administration could correct bleeding. The therapeutic potential of FXa is limited, however, due to its very short plasma half-life and potential for inducing excessive coagulation due to activation of other coagulation factors.

Earlier work identified a FXa variant (I16L variant) in which leucine replaced isoleucine at the amino-terminus of the wild-type FXa heavy chain (position 16 in the chymotrypsin numbering scheme). The substitution yielded a FXa variant with zymogen-like characteristics. Toso, R., et al., The conformational switch from the factor X zymogen to protease state mediates exosite expression and prothrombinase assembly. J. Biol. Chem. 283, 18627-18635 (2008); Ivanciu L., et al., A zymogen-like factor Xa variant corrects the coagulation defect in hemophilia. Nat. Biotechnol. 29:1028-33 (2011).

When not incorporated into the prothrombinase complex with its cofactor Factor Va (FVa), the FXa I16L variant had no significant catalytic activity and was better protected from inactivation by serum protease inhibitors compared to wild-type FXa. As a result, the variant had longer serum half-life compared to wild-type FXa. Binding to FVa in prothrombinase, however, caused the variant to transition from the zymogen-like state to the active conformation, thereby restoring the ability of the variant to catalyze conversion of prothrombin to thrombin and thus its procoagulant activity. In mouse models of hemophilia A and hemophilia B, administering the FXa I16L variant before injury reduced blood loss following tail-clipping in a dose dependent manner. The results of these experiments suggest that the FXa I16L variant might be useful to treat uncontrolled bleeding in humans with hemophilia.

The FXa I16L variant used in the earlier studies, however, was made in small quantities from stably transfected HEK 293 cells followed by activation of the FX protein using Russell's viper venom protease (abbreviated "RVVX"). Toso, R., Zhu, H. & Camire, R.M. The conformational switch from the factor X zymogen to protease state mediates exosite expression and prothrombinase assembly. J. Biol. Chem. 283, 18627-18635 (2008). While useful for small-scale studies, this approach is not suitable for production of large quantities of purified FXa variant protein required for clinical studies and eventual supply to patients. Accordingly, there is a need in the art for preparations of the FXa I16L variant protein made in such quantity and purity that they may be tested in clinical trials, and once approved, provided to subjects in need of hemostasis.

SUMMARY OF THE INVENTION

The present disclosure addresses the unmet need in the art described above by providing compositions of FXa variant proteins produced in sufficient purity and quantity that they can be supplied to subjects in need of hemostasis. In various embodiments, these compositions comprise different isoforms and post-translational modifications of FXa variant proteins.

In one embodiment, compositions comprise the beta form of FXa variant protein in which the light and heavy chain protein sequences respectively consist of amino acids 1 to 139 and 146 to 386, amino acids 1 to 140 and 146 to 384, amino acids 1 to 140 and 146 to 386, amino acids 1 to 141 and 146 to 384, amino acids 1 to 141 and 146 to 386, amino acids 1 to 142 and 146 to 384, amino acids 1 to 142 and 146 to 386, amino acids 1 to 143 and 146 to 384, and amino acids 1 to 143 and 146 to 386, all of the amino acid sequence of SEQ ID NO:1.

In another embodiment, compositions comprise the alpha form of FXa variant protein in which the light and heavy chain protein sequences respectively consist of amino acids 1 to 139 and 146 to 398, amino acids 1 to 140 and 146 to 398, amino acids 1 to 140 and 146 to 399, amino acids 1 to 141 and 146 to 398, amino acids 1 to 141 and 146 to 399, amino acids 1 to 142 and 146 to 398, and amino acids 1 to 142 and 146 to 399, all of the amino acid sequence of SEQ ID NO:1.

In any one or more of the beta and alpha isoform embodiments of the FXa variant proteins described above, the light chains of the proteins can be modified to include β-hydroxy Asp$^{63}$, an O-linked hexose and 9, 10 or 11 Gla residues. In some embodiments, 9 Gla residues are present. In other embodiments, 10 Gla residues are present. And in yet other embodiments, 11 Gla residues are present.

In any one or more of the beta isoform embodiments of the FXa variant proteins described above, the heavy chains can be modified to include one or two core-1 O-linked glycans. In some embodiments, only the first, only the second, or both core-1 O-linked glycans can be non-sialylated, mono-sialylated or di-sialylated. According to some embodiments, no sialic acid groups are present. In other embodiments, one sialic acid group is present. In yet other embodiments, two sialic acid groups are present. In further embodiments, three sialic acid groups are present. And in yet further embodiments, a total of four sialic acid groups are present.

According to some embodiments, FXa variant protein compositions include at least one FXa variant protein species listed in Table 2 of the disclosure. In other embodiments, compositions of the disclosure comprise at least 5, at least 10, at least 15, at least 20, at least 25, at least 30, at least 35, at least 40, at least 45, at least 50, at least 55, or at least 60 of the FXa variant protein species listed in Table 2.

According to other embodiments, FXa variant protein compositions include at least one FXa variant protein in which the light chain is a species listed in Table 3 of the disclosure. And in yet other embodiments, FXa variant protein compositions include at least one FXa variant protein in which the heavy chain is a species listed in Table 4 of the disclosure.

In some embodiments, any one or more of the FXa variant proteins of the disclosure can be present in a composition at an average abundance that varies relative to other species that may be present. For example, a particular species may be present at major, minor or trace abundance compared to other species that are present. Alternatively, a particular species may be present at high abundance, medium abundance, low abundance, or very low abundance compared to other species that are present.

The present disclosure also provides nucleic acids, vectors, host cells and methods of making and purifying FXa variant proteins.

Included, for example, are nucleic acid sequences encoding FX variant protein including a replacement of the native Activation Peptide (AP) sequence with a PACE processing site, thereby permitting intracellular activation of the clotting factor. In some embodiments, the AP sequence is removed entirely and replaced with the amino acid sequence Arg-Lys-Arg. According to some embodiments, a cDNA sequence encoding FX variant protein is provided by the nucleic acid sequence of SEQ ID NO:4, and the amino acid sequence encoded thereby is provided by the amino acid sequence of SEQ ID NO:1. Related methods are provided for making FXa variant protein by growing host cells co-expressing paired basic amino acid cleaving enzyme (abbreviated "PACED") (or a similar protease) and FX variant protein, and then purifying the FXa variant protein produced, processed and secreted by the host cells. Disclosed as well are FXa variant proteins produced according to these methods. In some embodiments of these methods, host cells are CHO cells.

Purification of FXa variant proteins can be performed by chromatography, including passing a solution comprising the proteins through a mixed mode chromatography (MMC) column (e.g., using Capto MMC media), followed by washing and eluting, then passing the proteins through a first ion exchange chromatography column (e.g., using Q-Sepharose Fast Flow media), followed by washing and eluting, and then passing the proteins through a second different ion exchange chromatography column (e.g., using Fractogel $SO_3^-$ media), followed by washing and eluting. Other methods for purifying FXa variant proteins are also possible.

Purification methods can optionally include a step of viral inactivation, as well as the steps of ultrafiltration and diafiltration. After FXa variant proteins are purified, and in some instances concentrated, they can be diluted in a pharmaceutically acceptable diluent optionally containing other ingredients such as buffers or excipients.

The disclosure also provides methods of treating subjects in need of hemostasis by administering a hemostatically effective amount of a composition comprising one or more of the FXa variant proteins of the disclosure. In other embodiments, subjects are administered a hemostatically effective amount of a composition comprising one or more of the FXa variant proteins of the disclosure before bleeding occurs to prophylactically prevent uncontrolled bleeding in a susceptible subject. In some embodiments, the subject is treated for Hemophilia A. In other embodiments, the subject is treated for Hemophilia B. And in yet other embodiments, the subject is treated for trauma or other types of uncontrolled bleeding.

BRIEF DESCRIPTION OF THE DRAWINGS

FIG. 1A provides the amino acid sequence (SEQ ID NO:1) of mature FX variant protein in which the wild-type isoleucine residue at position 146 is substituted with the leucine shown in bold. Position 146 corresponds to position 16 in the chymotrypsin numbering system. Potential γ-carboxyglutamic acid residues (Gla) are underlined and in italics. Predicted intrachain and interchain disulfide bonds are illustrated by lines drawn between the linked cysteines. The predicted β-hydroxylation site is enclosed by a box with solid lines. The PACE recognition and cleavage site engineered to replace the Activation Peptide is enclosed by a box with broken lines. The lysine forming the carboxy-terminal amino acid of the beta form of the heavy chain ($Lys^{386}$) is enclosed by an oval with solid line. FIG. 1B provides the predicted amino acid sequence (SEQ ID NO:2) of mature FX variant protein light chain. FIG. 1C provides the predicted amino acid sequence (SEQ ID NO:3) of the FXa variant protein heavy chain. FIG. 1D provides the nucleotide sequence (SEQ ID NO:4) of a cDNA encoding FX variant protein, including signal sequence and propeptide.

FIG. 7B provides the mass spectrum of FXa variant protein heavy chain after reduction and alkylation of a purified preparation of the protein. The mass spectrum demonstrates extensive mass heterogeneity attributable to presence of different types of post-translational modifications. Major peaks are identified in the figure by their observed mass in daltons. Peak assignments based on the mass spectrum after RP-HPLC/ESI-QTOF MS analysis were used to confirm the amino acid sequence of protein isoforms and to identify certain post-translational modifications as described in Table 4 and elsewhere herein. Peaks labeled with "*" indicates overalkylation of the heavy chain.

DETAILED DESCRIPTION

Figure 2:
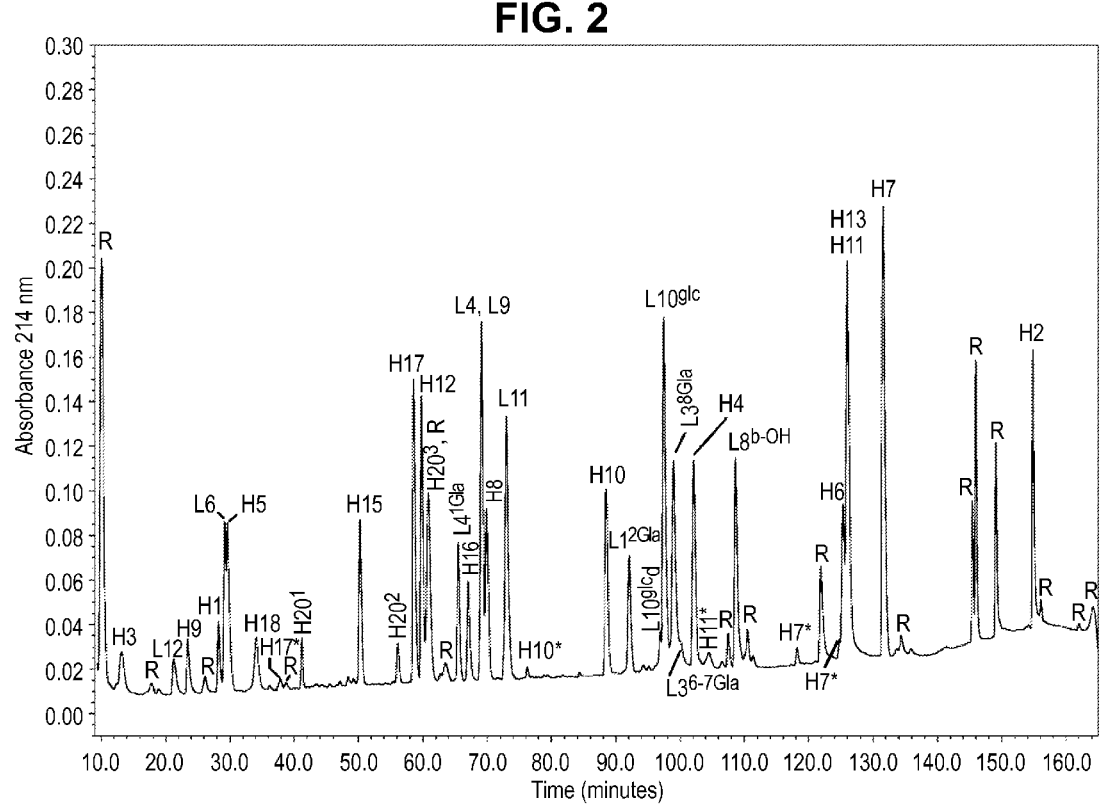
FIG. 2 provides the mass spectrum of peptides resulting from the reduction, alkylation, and proteolytic digestion with Lys-C of a purified preparation of intact FXa variant protein. Peak assignments based on the mass spectrum after RP-HPLC/ESI-QTOF MS analysis of peptides were used to confirm the amino acid sequence of the protein and to identify certain post-translational modifications described in Table 1 and elsewhere herein. Peak labeling is as follows. "L" followed by a number refers to a particular peptide derived from the light chain. "H" followed by a number refers to a particular peptide derived from the heavy chain. "$H20^1$": C-terminal alpha-form of H chain ending in $Lys^{399}$ containing two di-sialylated core-1 O-glycans. "$H20^2$": C-terminal alpha-form of H chain ending in $Lys^{399}$ containing one di-sialylated core-1 O-glycan. "$H20^3$": C-terminal alpha-form of H chain ending in $Leu^{398}$ containing one di-sialylated core-1 O-glycan. "$L4^{1Gla}$": L chain peptide #4 containing 1 γ-carboxyglutamic acid residue. "$L10^{glc}$": L chain peptide #10 containing potential O-linked glucose (hexose). "$L1^{2Gla}$": L chain peptide #1 with 2 γ-carboxyglutamic acid residues. "$L3^{6-8Gla}$": L chain peptide #3 with 6, 7 or 8 γ-carboxyglutamic acid residues. "$L8^{b-OH}$": L chain peptide #8 containing β-hydroxy Asp. "d": deamidation. "R": reagent peak, i.e., buffer related products consistent with reagent blank. "*": overalkylation.

Described herein are compositions comprising FXa variant protein produced in sufficient purity and quantity to be tested in clinical trials and provided to subjects in need of hemostasis. Also described are methods of making and purifying FXa variant protein.

In certain embodiments, the phrase "FX variant protein," "FXa variant protein," and similar terms refer (unless otherwise clear from context) to human Factor X (FX) or activated Factor X (FXa), respectively, in which the isoleucine (Ile or I) immediately following the Activation Peptide sequence in the heavy chain is substituted with leucine (Leu or L). Based on sequence alignment between the FXa heavy chain and the catalytic domain of chymotrypsin, this substitution is also referred to as the I16L substitution mutation using the chymotrypsin numbering scheme. This position corresponds to amino acid 146 in SEQ ID NO:1 and amino acid 1 in SEQ ID NO:3. As discussed above, FXa including this mutation has zymogenic properties that allow it to circulate in blood for longer periods of time compared to wild-type FXa, but is also capable of cleaving prothrombin at high rate when incorporated into the prothrombinase complex.

According to other embodiments, FX variant protein and FXa variant protein refer to human FX or FXa, respectively, in which the amino acid corresponding to position 146 in SEQ ID NO:1 (position 16 in chymotrypsin numbering scheme) is substituted with Phe (F), Asp (D), or Gly (G). According to yet other embodiments, FX variant protein and FXa variant protein refer to human FX or FXa, respectively, in which the valine (Val or V) corresponding to position 147 in SEQ ID NO:1 (position 17 in chymotrypsin numbering scheme) is substituted with Leu (L), Ala (A), or Gly (G). And, in other embodiments, FX variant protein and FXa variant protein refer to human FX or FXa, respectively, in which the amino acid corresponding to position 329 in SEQ ID NO:1 (position 194 in chymotrypsin numbering scheme) is substituted with Asn (N) or Glu (E).

Wild-type Factor X normally circulates in the blood as an inactive two-chain zymogen held together by a disulphide bond. The two-chain zymogen is formed from mature FX (i.e., lacking signal peptide and propeptide) after proteolytic removal of the peptide Arg-Lys-Arg present in the mature protein as amino acids 140-142. Activation, however, requires removal of the Activation Peptide (AP) by Factor IXa or Factor VIIa preliminary to clot formation, or by other proteases such as RVVX. The AP corresponds to amino acids 143-194 in mature single-chain FX. In the two-chain zymogen, it is present at the amino-terminal end of the heavy chain. M. Hertzberg, Biochemistry of factor X, Blood Rev. 8(1):56-62 (1994).

In an exemplary embodiment, Factor X variant protein sequence was modified by removing the Activation Peptide and replacing it with the amino acid sequence Arg-Lys-Arg (RKR in single letter code) to create a recognition and cleavage site for paired basic amino acid cleaving enzyme (PACE; also called furin). Rather than activating FXa in a separate step, AP replacement permits intracellular activation of FX variant protein when PACE is co-expressed in host cells. This avoids the need to first purify FX variant produced by cells, separately activate the protein using a protease (such as RVVX) and then purify variant FXa. By avoiding these extra steps, FXa variant can be produced in purer form and in greater quantities.

Figures 1B, 1C:
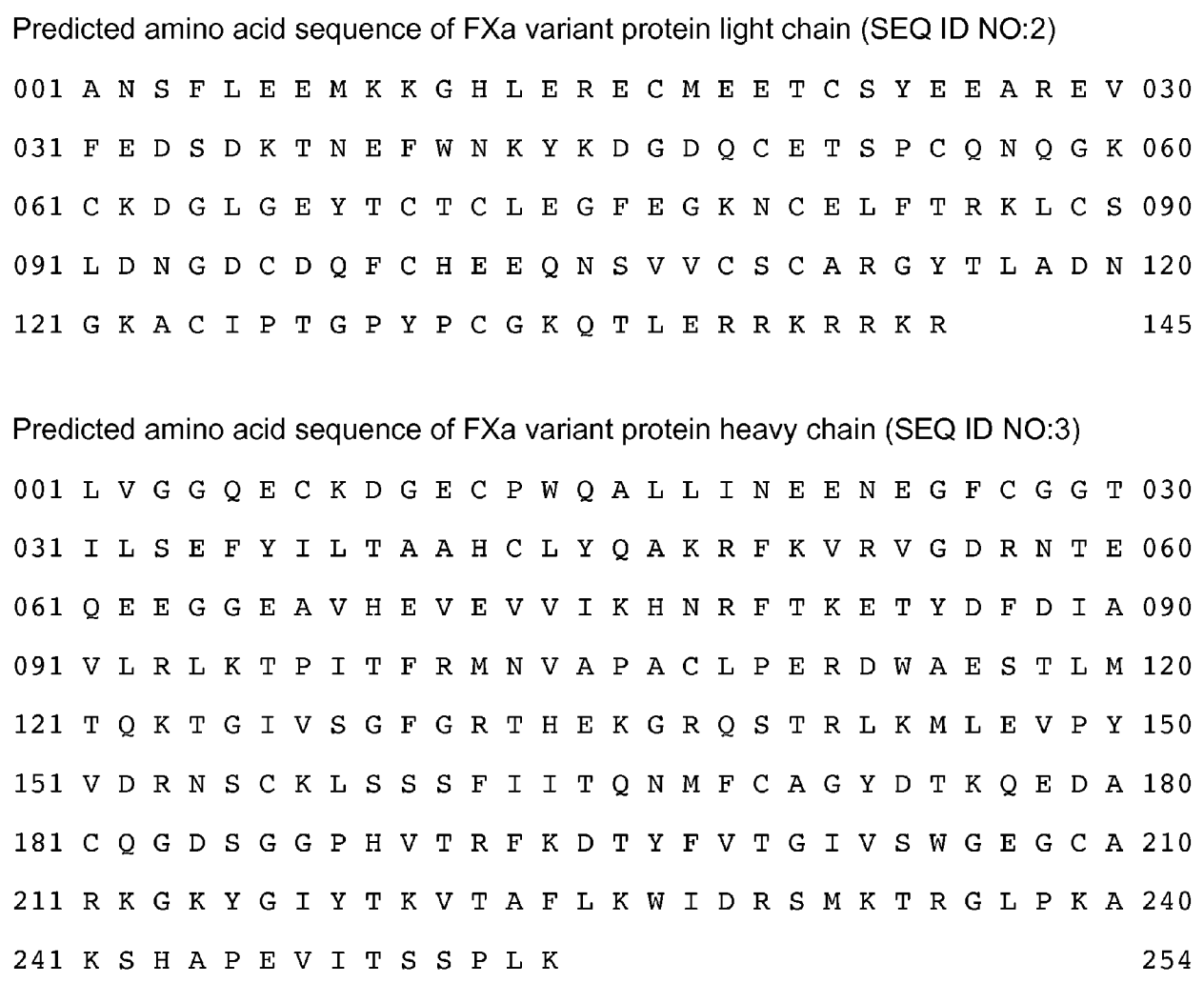

The mature Factor X variant amino acid sequence is depicted in FIG. 1A (SEQ ID NO:1) in which the I16L leucine substitution appears at amino acid position 146 (bold), the RKR sequence replacing the Activation Peptide appears at positions 143-145 and the PACE processing site appears at positions 140-145 (box with broken line). FIG. 1B and FIG. 1C depict the predicted amino acid sequence of the FXa variant light chain (SEQ ID NO:2) and heavy chain (SEQ ID NO:3), respectively, after cleavage at the PACE site.

Analysis of multiple preparations of FXa variant protein produced according to the methods of the disclosure demonstrated an unexpected degree of heterogeneity with respect protein sequence and post-translational modification compared to the predicted structure. Nevertheless, such compositions comprising structurally heterogeneous populations of FXa variant proteins were capable of acting as potent pro-coagulants in an in vitro assay. As described further below, the heterogeneity was attributable to variations in light chain and heavy chain amino acid sequence and post-translational modifications present in one, the other, or both chains.

Without wishing to be bound by any particular theory of operation, it is believed that one source of structural heterogeneity is attributable to variable cleavage at the PACE/furin protease recognition and cleavage site engineered to replace the Activation Peptide. In a non-limiting embodiment, the amino acid sequence of the PACE site is RKRRKR (SEQ ID NO:5) engineered into the FX variant protein by replacing the native AP amino acid sequence with the residues RKR which, in concert with the last three residues of the light chain, forms the proteolytic recognition site RKRRKR (SEQ ID NO:5). Other PACE recognition sites can be used as well (e.g., RKR alone), as could recognition and cleavage sites for proteases other than PACE/furin.

In some embodiments, the PACE site is proteolytically cleaved to remove it entirely from the light chain leaving no residues behind (ANS . . . TLER$^{139}$/RKRRKR/) (SEQ ID NO:6 and SEQ ID NO:5, respectively the light chain and a peptide fragment). In the foregoing and following embodiments described in this paragraph, slash marks ("/") indicate possible cleavage sites between the adjacent amino acids and the superscripted numeral indicates the position of the carboxy-terminal amino acid of the light chain after cleavage (based on FIG. 1A; SEQ ID NO:1). In other embodiments, the PACE site is proteolytically cleaved leaving its first residue at the C-terminus of the light chain (ANS . . . TLERR$^{140}$/KRRKR/) (SEQ ID NO:7 and SEQ ID NO:8, respectively the light chain and a peptide fragment). In other embodiments, the PACE site is proteolytically cleaved leaving its first two residues at the C-terminus of the light chain (ANS . . . TLERRK$^{141}$/RRKR/) (SEQ ID NO:9 and SEQ ID NO:10, respectively the light chain and a peptide fragment). In other embodiments, the PACE site is proteolytically cleaved leaving its first three residues at the C-terminus of the light chain (ANS . . . TLERRKR$^{142}$/RKR/) (SEQ ID NO:11). In other embodiments, the PACE site is proteolytically cleaved leaving its first four residues at the C-terminus of the light chain (ANS . . . TLERRKRR$^{143}$/KR/) (SEQ ID NO:12). In other embodiments, the PACE site is proteolytically cleaved leaving its first five residues at the C-terminus of the light chain (ANS . . . TLERRKRRK$^{144}$/R/) (SEQ ID NO:13). And in yet other embodiments, the PACE site is proteolytically cleaved leaving its entire sequence at the C-terminus of the light chain (ANS . . . TLERRKRRKR$^{145}$/) (SEQ ID NO:2).

In other embodiments, structural heterogeneity in the light chain can also include presence of varying number of Gla residues in the Gla domain attributable to variations in the degree of γ-carboxylation of certain glutamic acid residues. In certain embodiments, the number of Gla residues is 9, 10, or 11. Potential sites of glutamic acid γ-carboxylation in the Gla domain are identified in FIG. 1A. According to other embodiments, additional potential sources of light chain structural heterogeneity include presence or absence of a β-hydroxylated aspartic acid residue at Asp$^{63}$ (FIG. 1A; SEQ ID NO:1) and presence or absence of an O-linked hexose. In some embodiments, the O-linked hexose is glucose, but in other embodiments it may be a different aldohexose, or a cyclic hemiacetal, ketohexose, or other O-linked hexose.

The heavy chain can also exhibit structural heterogeneity. According to certain embodiments variation can occur in the length of the heavy chain. For example, some heavy chains are the longer alpha isoform terminating at K$^{399}$ (SEQ ID NO:3) (the superscripted numeral indicating the position of the carboxy-terminal amino acid of the heavy chain based on FIG. 1A; SEQ ID NO:1), but in other instances the terminal lysine is not present so that the protein ends at L$^{398}$ (SEQ ID NO:14). In other embodiments, the heavy chain is the shorter beta form terminating at K$^{386}$ or K$^{384}$ (SEQ ID NO:46 and SEQ ID NO:45, respectively).

Yet another source of heterogeneity in the heavy chains is the degree of O-linked glycosylation. Thus in some embodiments, the heavy chains are unglycosylated. In other embodiments, heavy chains include one or two core-1 O-glycans. A core-1 O-glycan is an O-glycan where N-acetylgalactosamine (GalNAc) is attached to serine or threonine and galactose (Gal) is attached to GalNAc. In some embodiments of the disclosure the GalNAc sugar is present but the Gal sugar is missing. According to yet other embodiments, each of the two core-1 O-linked glycans can separately be unsialylated, mono-sialylated or di-sialylated, such that heavy chains can possess 0-4 sialic acid groups in total. When sialic acid groups are present, they can be attached to either GalNAc or to Gal, or to both sugars.

According to other embodiments, different pairings of light chains and heavy chains are possible, thereby yielding a large combinatorial set of two-chain zymogens with different chain lengths and post-translational modifications.

In other embodiments, the different species of FXa variant proteins can vary in their relative abundance. In one embodiment, abundance of the various species can be detected by comparing peak heights in the mass spectra of intact FXa variant proteins. Alternatively, abundance of light and heavy chains can be separately analyzed by mass spectrometry after intact protein is reduced and alkylated to eliminate interchain and intrachain disulfide bonds. As described in the Examples, below, abundance of different FXa variant species can be scored as major, minor or trace by comparison to the highest peak in mass spectra.

Mass peak height comparison, however, is not the only method of measuring abundance. Other methods for measuring absolute or relative abundance of structural species is within the knowledge of those of ordinary skill in the art. In a non-limiting example of another method for categorizing relative abundance, a species is considered to be in high abundance if its mass spectrum peak height is at least about 50% that of the most abundant species (i.e., highest peak in a mass spectrum). A species is of medium abundance if its peak is between about 10-50% that of the most abundant species. A species is of low abundance if its peak is between about 2-10% that of the most abundant species, and is of very low abundance if its peak is less than about 2% that of the most abundant species. Other conventions for comparing relative species abundance are also possible.

Specific, non-limiting embodiments of structural heterogeneity in FXa variant protein light chains, heavy chains and combinations thereof are described below.

Embodiments of the disclosure include FXa variant proteins in which the carboxy-terminus of the light chain ends at different amino acids due to variable cleavage at the PACE site. Related embodiments include presence of varying numbers of Gla residues and post-translational modifications such as β-hydroxylation of an aspartic acid residue and an O-linked hexose. Some of these embodiments are described below.

In certain embodiments, compositions of the disclosure comprise a FXa variant protein in which the light chain consists of amino acids 1 to 139 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 140 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy $Asp^{63}$, an O-linked hexose, or both these post-translational modifications. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 141 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy $Asp^{63}$, an O-linked hexose, or both these post-translational modifications. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 142 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy $Asp^{63}$, an O-linked hexose, or both these post-translational modifications. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 143 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy $Asp^{63}$, an O-linked hexose, or both these post-translational modifications. Compositions of the disclosure may comprise any of the FXa variant proteins described in this paragraph alone or in combination with the others so described, as well as with any of the other FXa variant proteins of the disclosure.

Embodiments of the disclosure include FXa variant proteins in which the carboxy-terminus of the heavy chain ends at different amino acids. Related embodiments include varying numbers of O-linked glycans including varying degrees of sialylation. Some of these embodiments are described below.

In certain embodiments, compositions of the disclosure comprise a FXa variant protein in which the heavy chain consists of amino acids 146 to 384 of the amino acid sequence of SEQ ID NO:1. Compositions of the disclosure may further comprise any of the other FXa variant proteins of the disclosure.

In certain embodiments, compositions of the disclosure comprise a FXa variant protein in which the heavy chain consists of amino acids 146 to 386 of the amino acid sequence of SEQ ID NO:1. Compositions of the disclosure may further comprise any of the other FXa variant proteins of the disclosure.

In certain embodiments, compositions of the disclosure comprise a FXa variant protein in which the heavy chain consists of amino acids 146 to 398 of the amino acid sequence of SEQ ID NO:1. In related embodiments, the heavy chain additionally comprises one core-1 glycan, which may be non-sialylated, mono-sialylated, or di-sialylated, or two core-1 glycans, each of which may independently be non-sialylated, mono-sialylated, or di-sialylated. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the heavy chain consists of amino acids 146 to 399 of the amino acid sequence of SEQ ID NO:1. In related embodiments, the heavy chain additionally comprises one core-1 glycan, which may be non-sialylated, mono-sialylated, or di-sialylated, or two core-1 glycans, each of which may independently be non-sialylated, mono-sialylated, or di-sialylated. Compositions of the disclosure may comprise any of the FXa variant proteins described in this paragraph alone or in combination with the others so described, as well as with any of the other FXa variant proteins of the disclosure.

Embodiments of the disclosure include FXa variant proteins in which the carboxy-terminus of the light chain ends at different amino acids due to variable cleavage at the PACE site and in which the carboxy-terminus of the heavy chain also ends at different amino acids. Related embodiments include varying numbers of Gla residues and post-translational modifications, such as β-hydroxylation of an aspartic acid residue and an O-linked hexose in the light chains, and varying numbers of O-linked glycans including varying degrees of sialylation in the heavy chains. Some of the these embodiments are described below.

In certain embodiments, compositions of the disclosure comprise a FXa variant protein in which the light chain consists of amino acids 1 to 139 of the amino acid sequence of SEQ ID NO:1 and the heavy chain consists of amino acids 146 to 384 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy $Asp^{63}$, an O-linked hexose, or both these post-translational modifications. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 139 of the amino acid sequence of SEQ ID NO:1 and the heavy chain consists of amino acids 146 to 386 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy $Asp^{63}$, an O-linked hexose, or both these post-translational modifications. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 139 of the amino acid sequence of SEQ ID NO:1 and the heavy chain consists of amino acids 146 to 398 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. In other related embodiments, the heavy chain additionally comprises one core-1 glycan, which may be non-sialylated, mono-sialylated, or di-sialylated, or two core-1 glycans, each of which may independently be non-sialylated, mono-sialylated, or di-sialylated. In yet other related embodiments, each possible permutation of post-translational modifications of the light chain is combined with each possible permutation of post-translational modifications of the heavy chain. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 139 of the amino acid sequence of SEQ ID NO:1 and the heavy chain consists of amino acids 146 to 399 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. In other related embodiments, the heavy chain additionally comprises one core-1 glycan, which may be non-sialylated, mono-sialylated, or di-sialylated, or two core-1 glycans, each of which may independently be non-sialylated, mono-sialylated, or di-sialylated. In yet other related embodiments, each possible permutation of post-translational modifications of the light chain is combined with each possible permutation of post-translational modifications of the heavy chain. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 140 of the amino acid sequence of SEQ ID NO:1 and the heavy chain consists of amino acids 146 to 384 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 140 of the amino acid sequence of SEQ ID NO:1 and the heavy chain consists of amino acids 146 to 386 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 140 of the amino acid sequence of SEQ ID NO:1 and the heavy chain consists of amino acids 146 to 398 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. In other related embodiments, the heavy chain additionally comprises one core-1 glycan, which may be non-sialylated, mono-sialylated, or di-sialylated, or two core-1 glycans, each of which may independently be non-sialylated, mono-sialylated, or di-sialylated. In yet other related embodiments, each possible permutation of post-translational modifications of the light chain is combined with each possible permutation of post-translational modifications of the heavy chain. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 140 of the amino acid sequence of SEQ ID NO:1 and the heavy chain consists of amino acids 146 to 399 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. In other related embodiments, the heavy chain additionally comprises one core-1 glycan, which may be non-sialylated, mono-sialylated, or di-sialylated, or two core-1 glycans, each of which may independently be non-sialylated, mono-sialylated, or di-sialylated. In yet other related embodiments, each possible permutation of post-translational modifications of the light chain is combined with each possible permutation of post-translational modifications of the heavy chain. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 141 of the amino acid sequence of SEQ ID NO:1 and the heavy chain consists of amino acids 146 to 384 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 141 of the amino acid sequence of SEQ ID NO:1 and the heavy chain consists of amino acids 146 to 386 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 141 of the amino acid sequence of SEQ ID NO:1 and the heavy chain consists of amino acids 146 to 398 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. In other related embodiments, the heavy chain additionally comprises one core-1 glycan, which may be non-sialylated, mono-sialylated, or di-sialylated, or two core-1 glycans, each of which may independently be non-sialylated, mono-sialylated, or di-sialylated. In yet other related embodiments, each possible permutation of post-translational modifications of the light chain is combined with each possible permutation of post-translational modifications of the heavy chain. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 141 of the amino acid sequence of SEQ ID NO:1 and the heavy chain consists of amino acids 146 to 399 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. In other related embodiments, the heavy chain additionally comprises one core-1 glycan, which may be non-sialylated, mono-sialylated, or di-sialylated, or two core-1 glycans, each of which may independently be non-sialylated, mono-sialylated, or di-sialylated. In yet other related embodiments, each possible permutation of post-translational modifications of the light chain is combined with each possible permutation of post-translational modifications of the heavy chain. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 142 of the amino acid sequence of SEQ ID NO:1 and the heavy chain consists of amino acids 146 to 384 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 142 of the amino acid sequence of SEQ ID NO:1 and the heavy chain consists of amino acids 146 to 386 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 142 of the amino acid sequence of SEQ ID NO:1 and the heavy chain consists of amino acids 146 to 398 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. In other related embodiments, the heavy chain additionally comprises one core-1 glycan, which may be non-sialylated, mono-sialylated, or di-sialylated, or two core-1 glycans, each of which may independently be non-sialylated, mono-sialylated, or di-sialylated. In yet other related embodiments, each possible permutation of post-translational modifications of the light chain is combined with each possible permutation of post-translational modifications of the heavy chain. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 142 of the amino acid sequence of SEQ ID NO:1 and the heavy chain consists of amino acids 146 to 399 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. In other related embodiments, the heavy chain additionally comprises one core-1 glycan, which may be non-sialylated, mono-sialylated, or di-sialylated, or two core-1 glycans, each of which may independently be non-sialylated, mono-sialylated, or di-sialylated. In yet other related embodiments, each possible permutation of post-translational modifications of the light chain is combined with each possible permutation of post-translational modifications of the heavy chain. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 143 of the amino acid sequence of SEQ ID NO:1 and the heavy chain consists of amino acids 146 to 384 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 143 of the amino acid sequence of SEQ ID NO:1 and the heavy chain consists of amino acids 146 to 386 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 143 of the amino acid sequence of SEQ ID NO:1 and the heavy chain consists of amino acids 146 to 398 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. In other related embodiments, the heavy chain additionally comprises one core-1 glycan, which may be non-sialylated, mono-sialylated, or di-sialylated, or two core-1 glycans, each of which may independently be non-sialylated, mono-sialylated, or di-sialylated. In yet other related embodiments, each possible permutation of post-translational modifications of the light chain is combined with each possible permutation of post-translational modifications of the heavy chain. Compositions of the disclosure may comprise any of the FXa variant proteins described in this paragraph alone or in combination with the others so described, as well as with any of the other FXa variant proteins of the disclosure.

In certain embodiments, compositions of the disclosure comprise a FXa variant protein in which the light chain consists of amino acids 1 to 143 of the amino acid sequence of SEQ ID NO:1 and the heavy chain consists of amino acids 146 to 399 of the amino acid sequence of SEQ ID NO:1. In related embodiments, the light chain additionally comprises 9 Gla residues, 10 Gla residues, or 11 Gla residues. In each of these embodiments, the light chain may further comprise β-hydroxy Asp$^{63}$, an O-linked hexose, or both these post-translational modifications. In other related embodiments, the heavy chain additionally comprises one core-1 glycan, which may be non-sialylated, mono-sialylated, or di-sialylated, or two core-1 glycans, each of which may independently be non-sialylated, mono-sialylated, or di-sialylated. In yet other related embodiments, each possible permutation of post-translational modifications of the light chain is combined with each possible permutation of post-translational modifications of the heavy chain. Compositions of the disclosure may comprise any of the FXa variant proteins described in this paragraph alone or in combination with the others so described, as well as with any of the other FXa variant proteins of the disclosure.

The present disclosure further provides isolated nucleic acids comprising nucleic acid sequences that encode FX variant protein. According to an exemplary, non-limiting embodiment, a complementary DNA sequence (cDNA) encoding FX variant protein is disclosed herein as SEQ ID NO:4. As will be appreciated by those of ordinary skill, many other nucleic acid sequences encoding FX variant protein are possible in light of the degeneracy of the genetic code.

In some embodiments, nucleic acid encoding FX variant protein can be provided with a sequence encoding a signal peptide and/or propeptide (i.e., leader sequences) positioned at the amino-terminus of the FX protein which, among other potential functions, directs newly synthesized protein to the secretory compartment. Post-translational processing then removes the leader before mature protein is secreted from the cell. In some embodiments, these sequences are derived from native human FX. Non-native leader sequences can be used, such as that from human prothrombin. Leader sequences from other proteins (including of non-human origin) can be used as well. In the embodiment of the nucleic acid sequence of SEQ ID NO:4, the amino-terminal leader sequence is from human prothrombin.

According to other embodiments, nucleic acid encoding FX variant protein can be modified to permit intracellular activation of the clotting factor to yield FXa variant proteins.

As noted above, FX normally circulates as a two-chain zymogen in which a 52 amino acid Activation Peptide is positioned at the amino-terminus of the FX heavy chain. Activation to form FXa capable of functioning as procoagulant in the prothrombinase complex requires proteolytic removal of the AP by proteases from the intrinsic or extrinsic clotting system, such as activated FIX or activated FVII. In prior studies, analogous methods of activation were used. Specifically, FX variant protein was expressed in cells and then activated in a separate step by treatment with Russell's Viper venom (RVVX) after which FXa variant protein was purified for subsequent analysis.

Although activated FX variant protein could in principle be produced at industrial scale using similar methods, doing so would be very inefficient and expensive. For example, rigorous purification to eliminate any residual RVVX would be required. To avoid these disadvantages, the native AP can be removed and replaced with recognition and cleavage sites of proteases capable of being expressed and functioning intracellularly. In this manner, it is possible for FX variant protein to be activated intracellularly without need for additional process steps. Activated FX variant proteins secreted by host cells into the growth medium can then be purified.

A non-limiting example of a nucleic acid sequence encoding FX variant in which the AP sequence is replaced with a PACE recognition and cleavage site is provided in SEQ ID NO:4. The protein sequence of the mature FX variant protein encoded by this exemplary cDNA sequence is provided in SEQ ID NO:1. In these embodiments, the amino acids constituting the AP (amino acids 143 to 194 of the wild-type FX protein sequence) are replaced with the sequence Arg-Lys-Arg (RKR in single letter code). This sequence, combined with the last three residues of the light chain sequence (also RKR; amino acids 140-142 of SEQ ID NO:1) creates a recognition and cleavage site (i.e., RKRRKR) (SEQ ID NO:5) for paired basic amino acid cleaving enzyme (PACE). Soluble PACE enzyme co-expressed in the same host cells expressing the modified FX variant protein can therefore activate the clotting factor intracellularly.

In some embodiments, where host cells natively express an enzyme with a similar recognition site as PACE, it may not be necessary to co-express an exogenous protease. Rather, the native protease may be sufficient to activate FX variant protein expressed in the cells, thereby producing and secreting activated FX variant protein.

In other embodiments, recognition and cleavage sites for proteases different than PACE, but also capable of functioning intracellularly, can be used to replace the AP amino acid sequence. Such enzymes can be co-expressed in the same host cells as FX variant protein to activate the modified clotting factor. If native enzymes capable of cleaving the engineered site are produced at sufficient levels in the host cells, co-expression of exogenous proteases may not be required.

Nucleic acid sequences encoding FX variant proteins of the present disclosure may be incorporated into vectors using techniques well known to those of ordinary skill in the art.

Vectors, in certain embodiments, include plasmids generally, bacterial plasmids, eukaryotic episomes, yeast artificial chromosomes and viral genomes. Exemplary non-limiting viruses include retroviruses, adenoviruses, adeno-associated viruses (AAV), and plant viruses such as cauliflower mosaic virus, and tobacco mosaic virus. Other types of vectors are possible. In some embodiments, vectors are capable of autonomous replication in suitable hosts. In other embodiments, vectors are maintained in hosts extrachomosomally or can become integrated into the host's genome allowing the vector to replicate with the host's genome. Vectors comprising a gene and control sequences sufficient to maintain transcription and translation of the gene are called expression vectors. Vectors according to the present disclosure may be selected or designed, according to the knowledge of those ordinarily skilled in the art, to function in any cell type capable of supporting expression of FX variant protein, including bacterial cells, other prokaryotic cells, yeast cells, other fungal cells, plant cells, animal cells, insect cells, mammalian cells, CHO cells, and human cells, or others.

Vectors may optionally contain one or more control sequences. Certain control sequences permit replication, such as origins of replication. Other control sequences control or modulate transcription, such as promoters, enhancers, and transcription termination sites. Non-limiting examples of promoter or enhancers are those derived from retroviral LTRs, cytomegalovirus (CMV), Simian Virus 40 (SV40), adenovirus (e.g., the adenovirus major late promoter (AdMLP)), or polyoma virus. Additional examples include tissue specific promoters and enhancers, constitutively active promoters and enhancers, and inducible promoters and enhancers. Other promoters and enhancers are also possible. Yet other control sequences control or modulate post-transcriptional RNA processing, such as splicing and polyadenylation signals, or signals that increase or decrease mRNA stability. Other control sequences control or modulate protein translation, such as translation initiation sequences (e.g., Kozak consensus sequence), post-translational processing, or protein stability.

Vectors can also include selectable marker genes, permitting the selection of host cells that have taken up the vectors. Non-limiting examples include selectable marker genes that confer a drug-resistant phenotype, such as the dihydrofolate reductase gene (DHFR) (for use in DHFR⁻ host cells permitting selection using methotrexate), the neo gene (permitting selection with G418 or similar drugs), the hph gene (permitting selection with hygromycin B), and the glutamate synthetase gene (permitting selection with methionine sulfoximine).

Vectors comprising nucleic acid sequences encoding the FX variant proteins of the disclosure may be introduced into one or more types of host cells capable of supporting FX variant protein expression. Methods for introducing vectors into suitable host cells are well known to those of ordinary skill in the art. Non-limiting examples include transient and stable transfection, transformation, transduction and viral infection of target host cells. Other examples include dextran-mediated transfection, calcium phosphate precipitation, polybrene-mediated transfection, protoplast fusion, electroporation, encapsulation of the polynucleotide(s) in liposomes, and direct microinjection of the DNA into nuclei. Methods for transforming plant cells, bacterial and yeast cells are also well known in the art.

FX or FXa variant proteins can be expressed with other proteins to optimize expression or post-translational processing of FX or FXa variant proteins. In a non-limiting example, a vector including a gene encoding γ-glutamyl carboxylase can be co-transfected with the vector encoding FX variant protein into host cells to increase carboxylation of glutamic acids in the light chain Gla domain. By so doing, the extent of carboxylation and formation of Gla residues in the Gla domain can be increased, thereby improving the yield of active clotting factor produced by the cells. In another embodiment described above, FX variant protein modified to replace the native AP amino acid sequence with a PACE cleavage site can be co-expressed with soluble PACE enzyme in the same host cells. The co-expressed PACE can then cleave FX variant protein intracellularly to form activated FX variant protein which is thereafter secreted from the cell. As noted above, this approach avoids the need to activate FX variant protein in a separate step, which would otherwise be very inefficient and expensive.

Cells capable of expressing FX variant proteins, and other proteins useful for optimizing expression of FX variant protein in an active form, include mammalian cells. Mammalian cell lines suitable as hosts for protein expression are known in the art, including those derived from humans, rats, mice and other mammals. Exemplary non-limiting examples include certain immortalized cell lines available from the American Type Culture Collection (ATCC) or other sources, including Chinese hamster ovary (CHO) cells, NS0 cells, SP2 cells, HEK-293T cells, NIH-3T3 cells, HeLa cells, baby hamster kidney (BHK) cells, African green monkey kidney cells (e.g., COS, CV-1 or Vero cells), human hepatocellular carcinoma cells (e.g., HepG2), A549 cells, A431 cells, HeLa cells, L cells, BHK21 cells, HL-60 cells, U937 cells, HaK cells, Jurkat cells, and others. Use of other mammalian cells as host cells for protein expression is possible according to the knowledge of those ordinarily skilled.

In other embodiments, cell lines from insects, plants, bacteria or fungi may be used. Exemplary non-limiting insect cells include Sf9 or Sf21 cells, which are often used in conjunction with the baculovirus vector expression system. Exemplary non-limiting plant cells include those from *nicotiana, arabidopsis,* duckweed, corn, wheat, and potato species. Exemplary non-limiting bacteria include *Escherichia coli, Bacillus subtilis, Salmonella typhimurium,* and *Streptomyces* strains. Exemplary non-limiting fungi include *Schizosaccharomyces pombe, Saccharomyces cerevisiae, Pichia pastoris, Kluyveromyces* yeast strains, and *Candida* yeast strains. Use of other insect, plant, bacterial and fungal cells as host cells for protein expression is possible according to the knowledge of those ordinarily skilled in the art.

Methods, reagents and conditions for culturing host cells to produce activated FX variant protein are within the knowledge of those ordinarily skilled in the art and are not intended to be limiting. In a non-limiting example, FXa variant proteins can be produced in 500 liter cultures of serum free medium supplemented with vitamin K. In another non-limiting example, FXa variant proteins of the disclosure can be produced at industrial scale, for example, in 2500 liter fermentation tanks, or even larger volumes, under conditions designed to optimize expression and recovery.

After growing host cells under culture conditions supporting expression and intracellular activation of FX variant proteins, the cellular growth medium can be processed to isolate and purify FXa variant proteins secreted during cell growth. In other embodiments, particularly when other than mammalian host cells are used, FXa variant protein remaining in cells can be released, for example, by breaking open cells mechanically, enzymatically, or with detergents.

Cell culture medium can be centrifuged and/or filtered to remove cells and debris, for example by depth filtration alone or followed by membrane filtration, for example through a membrane filter with average pore size of 0.45 μm, 0.2 μm, or some other pore size. After removing cellular debris by centrifugation and/or filtration, medium can be processed to further purify FXa variant proteins. Depending on the subsequent purification steps, dilution and/or buffer exchange of the clarified supernatant or filtrate may be desirable.

Methods for protein purification are well known in the art. Exemplary non-limiting methods of protein purification include salt precipitation, size exclusion chromatography, ion exchange chromatography, and affinity chromatography. For example, antibodies specifically recognizing FXa variant protein can be immobilized to purification columns to reversibly capture the protein from the surrounding medium or buffer. After washing the affinity column to remove contaminants, bound FXa variant protein can thereafter be eluted.

Partially purified FXa variant protein can be subjected to processing steps in accordance with good manufacturing practice or other regulatory requirements including, for example, removal or inactivation of viruses. Viruses can be removed by ultrafiltration or inactivated by treating a sample with alcohol and/or detergent, according to the knowledge of those ordinarily skilled in the art. For example, Virosart® brand virus filters, available from Sartorius Stedim Biotech, can be used, as can filters from other manufacturers. Other methods for removing or inactivating viruses are possible.

In some embodiments, mixed mode chromatography (MMC) can be used to purify FXa variant protein alone, or in combination with other purification steps. MMC, also called multimodal chromatography, refers to use of chromatography media that provides more than one type of interaction between ligand and sample components. Exemplary types of interactions include electrostatic (anionic or cationic exchanger), hydrophobic, pi-pi interaction, hydrogen bonding and thiophilic interaction. These interactions can cooperate or work independently. Specific, non-limiting examples of MMC media include Capto adhere, Capto adhere ImpRes, Capto MMC, Capto MMC ImpRes, Capto Core 700, all of which are described further in the Multimodal Chromatography Handbook published by GE Healthcare Life Sciences (2013). Capto MMC, for example, provides thiophilic, hydrophobic, hydrogen bonding, as well as cationic exchanger electrostatic properties. Use of MMC media from other sources is possible as well.

In some embodiments, ion exchange chromatography can be used to purify FXa variant protein alone, or in combination with other purification steps. Ion exchange chromatography refers to use of chromatography media allowing separation of molecules on the basis of differences in their net surface charge, which can vary with pH, salt and other conditions. At a pH above a protein's isoelectric point, the protein will bind to a positively charged medium (anion exchanger), whereas at a pH below its isoelectric point, a protein will bind to a negatively charged medium (cation exchanger). Ion exchange media and buffer conditions (e.g., salt concentration, pH, etc.) can be chosen so that a protein to be purified (e.g., a FXa variant protein) binds preferentially to the media, permitting contaminants that bind less strongly under the same conditions to be washed away, after which the protein of interest can be eluted from the chromatography column. Additional information about ion exchange chromatography is described further in the Ion Exchange Chromatography & Chromatofocusing Principles and Methods Handbook published by GE Healthcare (2010).

Ion exchangers can be categorized as strong or weak, which indicates the degree to which they remain charged as pH changes. Strong exchangers remain charged across a wide pH range, whereas weak exchangers do not. Examples of anion exchanger functional groups include quaternary ammonium (Q), which is strong, and diethylaminoethyl (DEAE) and diethylaminopropyl (ANX), which are considered weak. Examples of cation exchanger functional groups include sulfopropyl (SP) and methyl sulfonate (S), both of which are considered strong, and carboxymethyl (CM), which is weak.

In one embodiment, FXa variant protein can be purified using an anion exchange chromatography step alone, or followed by a cation exchange chromatography step. In another embodiment, FXa variant protein can be purified using a cation exchange chromatography step alone, or followed by an anion exchange chromatography step.

Specific, non-limiting examples of ion exchange media include Capto DEAE, Capto Q ImpRes, Capto SP ImpRes, Capto S, Capto Q, SOURCE 15Q, SOURCE 15S, SOURCE 30Q, SOURCE 30S, MacroCap SP, MacroCap Q, Mini Q PC, Mini S PC, Mini Q PE, Mini S PE, HR Mono Q, HR Mono S, PC Mono Q, PC Mono S, Mono Q GL, Mono S GL, DEAE Sephacel, CM Sephadex C-25, CM Sephadex C-50, DEAE Sephadex A-25, DEAE Sephadex A-50, QAE Sephadex A-25, QAE Sephadex A-50, SP Sephadex C-25, SP Sephadex C-50, ANX Sepharose 4 Fast Flow (High Sub), ANX Sepharose 4 Fast Flow (Low Sub), CM Sepharose Fast Flow, CM Sepharose High Performance, DEAE Sepharose CL-6B, DEAE Sepharose Fast Flow, Q Sepharose Big Beads, Q Sepharose Fast Flow, Q Sepharose High Performance, Q Sepharose XL, SP Sepharose Big Beads, SP Sepharose Big Beads Food Grade, SP Sepharose High Performance, SP Sepharose Fast Flow, and SP Sepharose XL, which are available from GE Healthcare. Other ion exchange media can be obtained from Merck Millipore including, for example, those in the Fractogel® series or the Eshmuno® series. Examples in the Fractogel® series include TMAE Resin, TMAE Hicap Resin, TMAE Medcap Resin, DEAE Resin, DMAE Resin, $SO3^-$ Resin, SE Hicap Resin, and $COO^-$ Resin. Examples in the Eshmuno® series include CPX, S, Q and HCX resins. Ion exchange media from other sources can be used as well.

After FXa variant protein has been sufficiently purified, the purified protein can be concentrated using ultrafiltration and diafiltration in preparation for packaging or further processing.

In some embodiments, purified and concentrated FXa variant proteins can be diluted in aqueous solutions containing buffers and other ingredients suitable for administration to subjects, and then packaged for long term storage until delivery. Additional processing steps can be employed. For example, compositions comprising FXa variant proteins, excipients, buffers, and other pharmaceutically acceptable ingredients can be lyophilized for long term storage.

FXa variant proteins of the disclosure, whether produced according to the methods described in the Examples below, or by other methods, can be analyzed to determine the presence and degree of structural heterogeneity using methods familiar to those of ordinary skill in the art.

For example, in some embodiments, intact protein or proteolytic fragments prepared therefrom, can be analyzed by direct protein sequencing, for example, using Edman degradation. Protein or peptides can also be analyzed by liquid chromatography (LC), including reverse phase LC (RP-LC), as well as mass spectrometry, including electrospray ionization quadrupole time-of-flight mass spectrometry (ESI-QTOF MS) to detect variation in amino acid sequence and the presence of particular post-translational modifications. In addition, the presence of charged groups, for example, γ-carboxylated glutamic acid residues (Gla) can be detected using anion exchange liquid chromatography (AEX-HPLC).

Where the presence of carbohydrate moieties suspected, their existence can be confirmed by removing them with specific glycosidases. Thereafter, treated protein, which should be devoid of the carbohydrate removed by the glycosidase, can be reanalyzed, for example, by mass spectrometry, to confirm the identity of the carbohydrate hypothesized to have been present.

Other analytical techniques familiar to those of ordinary skill in the art can be used to detect the extent and identity of structural heterogeneity in FXa variant proteins.

Compositions comprising FXa variant proteins of the disclosure can be tested for pro-coagulant activity. In a non-limiting example, clotting activity is measured with a one-stage clotting assay using Factor VIII deficient human plasma as substrate. One such assay is known as the activated partial thromboplastin time (APTT) assay, but other assays may be used according the knowledge of those ordinarily skilled in the art. APTT assay is described in more detail in Kamal, A. F., et al., How to interpret and pursue an abnormal prothrombin time, activated partial thromboplastin time, and bleeding time in adults, Mayo Clin Proc. 82(7):864-873 (2007).

In certain embodiments, compositions of the disclosure include a "therapeutically effective amount" or a "prophylactically effective amount" of FXa variant proteins. A "therapeutically effective amount" refers to an amount effective, at dosages and for periods of time necessary, to achieve a desired therapeutic result, for example hemostasis of uncontrolled bleeding. Therapeutically effective amount of the FXa variant may vary according to factors such as the disease state, age, sex, and weight of the individual, and the ability of the FXa variant to elicit a desired response in the individual. A therapeutically effective amount is also one in which any toxic or detrimental effects of the FXa variant are outweighed by the therapeutically beneficial effects. A "prophylactically effective amount" refers to an amount effective, at dosages and for periods of time necessary, to achieve a desired prophylactic result, for example, prevention of uncontrolled bleeding in a susceptible subject. For example, a dose may be given prior to a planned surgery. Examples of susceptible subjects include those with Hemophilia A or B, including those subjects producing inhibitory antibodies to factor replacement products.

Compositions of the disclosure can be administered to a subject, including a human patient, in need of treatment for or prevention of any condition characterized by insufficient coagulation or an excess of bleeding. Non-limiting examples of such conditions include Hemophilia A, Hemophilia B, Hemophilia A or B associated with inhibitory antibodies, coagulation factor deficiency, vitamin K epoxide reductase C1 deficiency, gamma-carboxylase deficiency, bleeding associated with trauma, injury, thrombosis, thrombocytopenia, stroke, coagulopathy, disseminated intravascular coagulation (DIC), over-anticoagulation treatment disorders, Bernard Soulier syndrome, Glanzman thrombasthenia, and storage pool deficiency. Treatment or prevention of other disorders characterized by insufficient coagulation or excess bleeding is also possible.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. According to some embodiments, parenteral compositions are formulated in dosage unit form for ease of administration and uniformity of dosage. Dosage unit form refers to physically discrete units to serve as unitary dosages for the subjects to be treated, with each unit containing a predetermined quantity of active compound calculated to produce the desired therapeutic effect in association with the appropriate pharmaceutical carrier.

In certain embodiments, a therapeutically or prophylactically effective amount of FXa variant proteins is about 0.0001 to 50 mg/kg, about 0.001 to 50 mg/kg, about 0.001 to 5 mg/kg, about 0.001 to 0.5 mg/kg, about 0.001 to 0.05 mg/kg, about 0.01 to 5 mg/kg or about 0.01 to 0.5 mg/kg. According to related embodiments, a therapeutically or prophylactically effective serum concentration of FXa variant proteins is about 0.0003 to 300 nM, about 0.003 to 300 nM, about 0.03 to 300 nM, about 0.003 to 30 nM, about 0.03 to 30 nM or about 0.3 to 3 nM. The serum concentration of the FXa variant may be measured by any method known in the art.

Unit doses of the compositions of the disclosure can be prepared to conveniently permit the administration of therapeutically or prophylactically effective amounts of FXa variant proteins to subjects or to achieve a desired serum concentration of such proteins in such subjects.

For any particular subject, specific dosage regimens or ranges may be adjusted over time according to the need of the subject being treated and the professional judgment of the individual responsible for administering or supervising the administration of the compositions. Accordingly, the dosage regimens and ranges set forth herein are exemplary only and are not intended to limit the scope or practice of the compositions of the disclosure.

Additionally provided are kits including, for example, one or more unit doses of a composition of the disclosure. Such unit doses can be in liquid form or as a lyophilisate. If the composition is packaged in lyophilized form, kits can additionally include a container filled with diluent, such as sterile water or saline solution, for resuspending the dried pellet. Kits can also include articles to be used for administration, including for example, hypodermic syringes, or tubing and butterfly needles, and the like. Kits can additionally include directions for use, alcohol pads for sterilizing skin, or other components.

Compositions comprising FXa variant protein may be administered once or multiple times until bleeding stops or adequate coagulation is achieved according to the knowledge of one of ordinary skill. Where multiple administrations are used, they may be hourly, daily, weekly or at other intervals. Administrations may be on a schedule such as every 10 minutes, every 15 minutes, every 20 minutes, every 30 minutes, every hour, every two hours, every three hours, every four hours, three times daily, twice daily, once daily, once every two days, once every three days, and once weekly. The FXa variant may also be administered continuously, e.g. via a minipump. The FXa variant may be administered via a parenteral route (e.g., intravenously, subcutaneously, intraperitoneally, or intramuscularly). The FXa variant may be administered once, twice, or more, or for at least the period of time required to achieve effective coagulation.

In another embodiment, compositions comprising FXa variant protein may be co-administered with another procoagulant including a different FXa variant (e.g., one having a different substitution at amino acid number 146 than leucine), Factor IX, Factor XIa, Factor XIIa, Factor VIII, Factor VIIa, FEIBA or prothrombin complex concentrate (PCC).

Compositions comprising FXa variant proteins may further comprise a pharmaceutically acceptable carrier or vehicle, which may be solvents, dispersion media, antibacterial and antifungal agents, isotonic and absorption delaying agents and the like that are physiologically compatible. Some examples of pharmaceutically acceptable carriers merely by way of illustration, are water, saline, phosphate buffered saline, dextrose, glycerol, ethanol and the like, as well as combinations thereof. Isotonifying agents, for example, salts (e.g., sodium chloride), sugars (e.g., sucrose), or polyalcohols (e.g., mannitol or sorbitol) can also be included in the composition. Additional examples of pharmaceutically acceptable substances are wetting agents, emulsifying agents, preservatives or buffers, which enhance the stability or other attributes of the instant compositions.

Compositions for use according to the disclosure may be in any suitable form for administration to a subject, for example, as a liquid for injection or for infusion. The form depends on the intended mode of administration and therapeutic application.

Therapeutic compositions are usually sterile and stable under the conditions of manufacture and storage. The composition can be formulated as a solution, microemulsion, dispersion, liposome, or other ordered structure suitable to high drug concentration. Sterile injectable solutions can be prepared by incorporating FXa variant proteins of the disclosure in the required amount in an appropriate solvent with one or a combination of ingredients described above, followed by filtered sterilization. In the case of sterile powders for the preparation of sterile injectable solutions, methods of preparation include vacuum drying or freeze drying (lyophilization) that yield a powder of the active ingredient plus any additional desired ingredient from a previously sterile filtered solution thereof.

The following examples are for illustrative purposes only and should not be construed as in any way limiting the scope of the claims or of other inventions disclosed herein.

EXAMPLES

Example 1

Expression and Purification of Recombinant FXa Variant Protein

Using standard molecular biology techniques and reagents, cDNA encoding FX variant protein including the I16L mutation was generated in which the native Factor X Activation Peptide amino acid sequence was replaced with the amino acid sequence RKR (single letter code) which, in concert with an RKR sequence at the C-terminus of the light chain, formed a PACE proteolytic cleavage site having the amino acid sequence RKRRKR (SEQ ID NO:5). The sequence of the cDNA and mature protein encoded thereby are described in FIG. 1D (SEQ ID NO:4) and FIG. 1A (SEQ ID NO:1), respectively. In this way, the FX precursor of the FXa variant could be activated by intracellular proteolytic cleavage by PACE enzymes co-expressed with the clotting factor. Additionally, the native signal sequence and propeptide of human FX were replaced with those of human prothrombin.

The cDNA encoding the FX variant was subcloned into an expression vector under the control of a constitutive promoter. The vector also expressed the neomycin resistance gene, permitting antibiotic selection of stable transfectants. A second vector was created to express the soluble form of the PACE enzyme.

CHO K1 host cells were adapted to grow in serum-free suspension and co-transfected by lipofection with the linearized vectors for expressing FXa variant and soluble PACE. Transfected cells were selected by growth in media supplemented with G418 antibiotic and Vitamin K1. Resistant clones were screened for recombinant FXa variant protein expression and activity. Clones exhibiting relatively high recombinant FXa variant protein expression and activity were adapted to growth in serum-free suspension culture. One clone was selected and used to establish a pre-master cell bank and then a master cell bank using chemically defined medium free of animal or human-derived components.

To produce drug substance for further study, cells expressing FXa variant were grown at 500 liter (L) or 2500 L scale using chemically defined media. To start, vials of cells from a cell bank were thawed, cultured, and progressively expanded by growth in vessels of increasing volume using a chemically defined, animal component-free medium. Once expansion was complete, cultures were maintained in small stirred tank bioreactors. For production, culturing was continued in 500 L or 2500 L scale bioreactors until harvest. To harvest, the cell culture medium was centrifuged to remove cells and debris. Medium was further clarified by depth filtration and filtration through a 0.2 μm filter.

The filtered medium was then diluted with buffer and loaded onto a Capto mixed mode chromatography (MMC) column (GE Healthcare Life Sciences). After washing, product was eluted from the column. The partially purified product was then diluted into a detergent solution for viral inactivation. After viral inactivation, product was loaded onto a Q-Sepharose Fast Flow Chromatography column (GE Healthcare Life Sciences), washed and eluted from the column. Eluted product was then diluted with buffer and loaded onto a Fractogel $SO_3^-$ Chromatography column (Merck Millipore), washed and eluted from the column. Eluted product was then filtered using Virosart® CPV filters (Sartorius Stedim Biotech) to remove any residual virus that might have been present. Following viral filtration, purified product was concentrated using ultrafiltration and diafiltration. Purified drug substance was then tested to characterize the FXa variant protein produced by the CHO cells.

Example 2

Terminal Amino Acid Sequence

Amino-terminal sequencing of FXa variant by Edman degradation was used to confirm the first ten residues of both the light chain amino-terminus and heavy chain amino-terminus. The analysis was performed by automated Edman degradation after FXa variant was resolved by SDS-PAGE under non-reducing and reducing conditions and electro-blotted onto a polyvinylidene difluoride (PVDF) membrane.

The light chain amino-terminal sequence was ANSFL(X)(X)MKK (single letter code) (SEQ ID NO:15). No signal occurred at residues 6 and 7 (shown as X), which is consistent with the presence of gamma carboxyglutamic acid (Gla) residues at those positions. The heavy chain amino-terminal sequence was LVGGQE(Z)KDG (SEQ ID NO:16). No signal occurred at residue 7 (shown as Z), which is consistent with the presence of cysteine at that position. These results confirmed the expected amino-terminal sequences of both the light chain and heavy chain compared to the theoretical sequence.

Example 3

Peptide Mapping to Confirm Primary Structure and Identify Post-Translational Modifications To confirm the primary amino acid sequence and to detect post-translational modifications, FXa variant protein produced as described in Example 1 was analyzed by peptide mapping. Specifically, the protein was reduced, alkylated, and digested with Lys-C lysyl endopeptidase (*Achromobacter lyticus* protease 1) after which the fragments were analyzed by reverse-phase high performance liquid chromatography/electrospray ionization quadrupole time-of-flight mass spectrometry (RP-HPLC/ESI-QTOF MS).

An example of the resulting peptide map profile is shown in FIG. 2 in which peptides are labeled according to their inferred relative positions in relation to the theoretical sequence of the light chain shown in FIG. 1B and the heavy chain shown in FIG. 1C. Peaks labeled with the letter "L" indicate a light chain peptide and those labeled with the letter "H" indicate a heavy chain peptide. Minor peaks representing buffer-related products are labeled "R". Several trace-level peaks representing deamidated (d) or overalkylated peptides are labeled "d" and "*", respectively.

The peptides detected by peptide mapping, their theoretical and observed masses, and amino acid sequences are shown in Table 1 below Amino acid numbering is based on FIG. 1A (SEQ ID NO:1).

TABLE 1

| Peptide | Residues | Theoretical Mass (Da) | Observed Mass (Da) | Confirmed Sequence | Experimental Observations |
|---|---|---|---|---|---|
| L1 + 2 Gla | 1-9 | 1155.475 | 1155.477 | ANSFLEEMK (SEQ ID NO: 17) | 2 Gla residues observed |
| L2 | 10 | 146.105 | | K | Not detected |
| L3 + 8 Gla | 11-36 | 3588.204 | 3588.208 | GHLERECMEETCSYEEAREVFEDSDK (SEQ ID NO: 18) | 8 Gla residues observed; 6 or 7 Gla residues also observed at trace levels. |
| L4 | 37-43 | 937.429 | 937.434 | TNEFWNK (SEQ ID NO: 19) | 0 Gla major species |
| L4 + 1 Gla | 37-43 | 981.419 | 981.419 | TNEFWNK (SEQ ID NO: 19) | 1 Gla minor species |
| L5 | 44-45 | 309.169 | | YK | Not detected |
| L6 | 46-60 | 1724.625 | 1724.625 | DGDQCETSPCQNQGK (SEQ ID NO: 20) | |
| L7 | 61-62 | 249.115 | | CK | Not detected |
| L8 + OH | 63-79 | 1952.766 | 1952.773 | DGLGEYTCTCLEGFEGK (SEQ ID NO: 21) | |
| L9 | 80-87 | 1067.507 | 1067.512 | NCELFTRK (SEQ ID NO: 22) | |
| L10 + Hex | 88-122 | 4245.634 | 4245.639 | LCSLDNGDCDQFCHEEQNSVVCSCARGYTLADNGK (SEQ ID NO: 23) | |
| L11 | 123-134 | 1321.568 | 1321.575 | ACIPTGPYPCGK (SEQ ID NO: 24) | |
| L12 | 135-141 | 929.541 | 929.542 | QTLERRK (SEQ ID NO: 25) | Also observed QTLERR (SEQ ID NO: 26) and QTLER (SEQ ID |

TABLE 1-continued

| Peptide | Residues | Theoretical Mass (Da) | Observed Mass (Da) | Confirmed Sequence | Experimental Observations |
|---|---|---|---|---|---|
| | | | | | NO: 27) as minor and trace species, respectively |
| H1 | 146-153 | 890.417 | 890.417 | LVGGQECK (SEQ ID NO: 28) | |
| H2 | 154-193 | 4620.081 | 4620.084 | DGECPWQALLINEENEGF CGGTILSEFYILTAAHCLYQAK (SEQ ID NO: 29) | |
| H3 | 194-196 | 449.275 | 449.276 | RFK | |
| H4 | 197-221 | 2777.394 | 2777.398 | VRVGDRNTEQEEGGEAV HEVEVVIK (SEQ ID NO: 30) | |
| H5 | 222-227 | 801.424 | 801.425 | HNRFTK (SEQ ID NO: 31) | |
| H6 | 228-240 | 1581.840 | 1581.843 | ETYDFDIAVLRLK (SEQ ID NO: 32) | |
| H7 | 241-268 | 3263.578 | 3263.581 | TPITFRMNVAPACLPERD WAESTLMTQK (SEQ ID NO: 33) | |
| H8 | 269-281 | 1387.721 | 1387.729 | TGIVSGFGRTHEK (SEQ ID NO: 34) | |
| H9 | 282-289 | 944.551 | 944.553 | GRQSTRLK (SEQ ID NO: 35) | |
| H10 | 290-302 | 1610.743 | 1610.746 | MLEVPYVDRNSCK (SEQ ID NO: 36) | |
| H11 | 303-321 | 2182.991 | 2182.992 | LSSSFIITQNMFCAGYDTK (SEQ ID NO: 37) | |
| H12 | 322-339 | 1988.865 | 1988.865 | QEDACQGDSGGPHVTRFK (SEQ ID NO: 38) | |
| H13 | 340-357 | 2045.952 | 2045.953 | DTYFVTGIVSWGEGCARK (SEQ ID NO: 39) | |
| H14 | 358-359 | 203.127 | | GK | Not detected |
| H15 | 360-365 | 743.385 | 743.385 | YGIYTK (SEQ ID NO: 40) | |
| H16 | 366-371 | 677.411 | 677.415 | VTAFLK (SEQ ID NO: 41) | |
| H17 | 372-378 | 934.469 | 934.470 | WIDRSMK (SEQ ID NO: 42) | |
| H18 | 379-384 | 670.413 | 670.413 | TRGLPK (SEQ ID NO: 43) | |
| H19 | 385-386 | 217.143 | | AK | Not detected |
| H20 | 387-399 | 2183.958 | 2183.956 | SHAPEVITSSPLK (SEQ ID NO: 44) | Observed with 1 and 2 di-sialylated O-glycans. Major form ends in Leu$^{398}$. Minor form ends in Lys$^{399}$. |

Theoretical masses were calculated with PAWS (Genomic Solutions, Ann Arbor, Mich.). Observed masses were calculated from the most abundant multiply-charged ion in the mass spectrum. All observed masses agreed with theoretical masses to within 10 ppm. Sequence coverage among the peptides for the light chain (LC) and heavy chain (HC) was approximately 94 and 98%, respectively. Three peptides from the L chain (L2, L5, L7) and two peptides from the heavy chain (H14, H19) were not detected. Calculated differences between theoretical and observed peptide mass permitted inference of the presence of certain post-translational modifications. Those residues found to be subject to modification are denoted by underlining in column 5 of Table 1.

The N-terminal Gla domain in the light chain contained between 9 and 11 total gamma carboxylated glutamic acid (Gla) residues. The major light chain species contained 10 Gla residues. Although peptide L1 was always carboxylated, heterogeneity was detected in peptides L3 and L4. Specifically, L3 peptide was observed with 6, 7, or 8 Gla residues and L4 peptide was observed with none or one Gla residue. See Table 1.

The heterogeneity as to gamma-carboxylation was confirmed using anion exchange high-performance liquid chromatography (AEX-HPLC) to measure charge heterogeneity. AEX-HPLC separation of FXa variant protein resolved isoforms containing 9, 10, and 11 gamma carboxyglutamic acid (Gla) residues. The relative frequency of the number of Gla residues within the FXa variant light chain was consistent among seven preparations of purified FXa variant protein tested. In particular, based on relative peak distributions, the frequency of occurrence of 9 Gla residues ranged from 10% to 17% (mean=12.1%, SD=2.5%), the frequency of occurrence of 10 Gla residues ranged from 41% to 46% (mean=43.0%, SD=1.8%) and the frequency of occurrence of 11 Gla residues ranged from 36% to 46% (mean=42.1%, SD=3.3%).

Purified 10 and 11 Gla isoforms were shown to be equally active in an APTT-based clotting assay, whereas the 9 Gla isoform had reduced activity (approximately 20% of the activity of the 10 and 11 Gla isoforms when normalized for mass).

Other post-translational modifications of the light chain were detected as well. In particular, the mass of peptide L8 was observed to be consistent with the presence of a beta-hydroxylated aspartic acid residue at position 63 ($Asp^{63}$) (SEQ ID NO:1). In addition, peptide L10 was observed with a mass difference indicating the addition of an O-linked hexose.

The heavy chain was also subject to O-linked glycosylation. In the peptide map, the major form of the heavy chain alpha isoform C-terminus was observed ending at amino acid $L^{398}$ and the minor form of the C-terminus was observed ending at amino acid $K^{399}$. Both of these peptides were observed containing one or two di-sialylated core-1 O-glycans, with the predominant species of both peptides containing one di-sialylated core-1 O-glycan. In the peptide map profile, the peak labeled "H20³" corresponds to the H20 peptide ending at $L^{398}$, and the peak labeled "H20²" corresponds to the H20 peptide ending at $K^{399}$, each containing one O-linked glycan. The peak labeled "H20¹" corresponds to the H20 peptide ending at $K^{399}$ and containing two O-linked glycans. An H20 peptide ending at $L^{398}$ having two O-linked glycans was detected at trace levels and is not labeled in FIG. 2. The O-glycans in H20 were localized to $Thr^{394}$ and $Ser^{395}$ by beta-elimination followed by MS fragmentation.

Example 4

Structural Heterogeneity Determined by High Performance Liquid Chromatography

Figure 3:
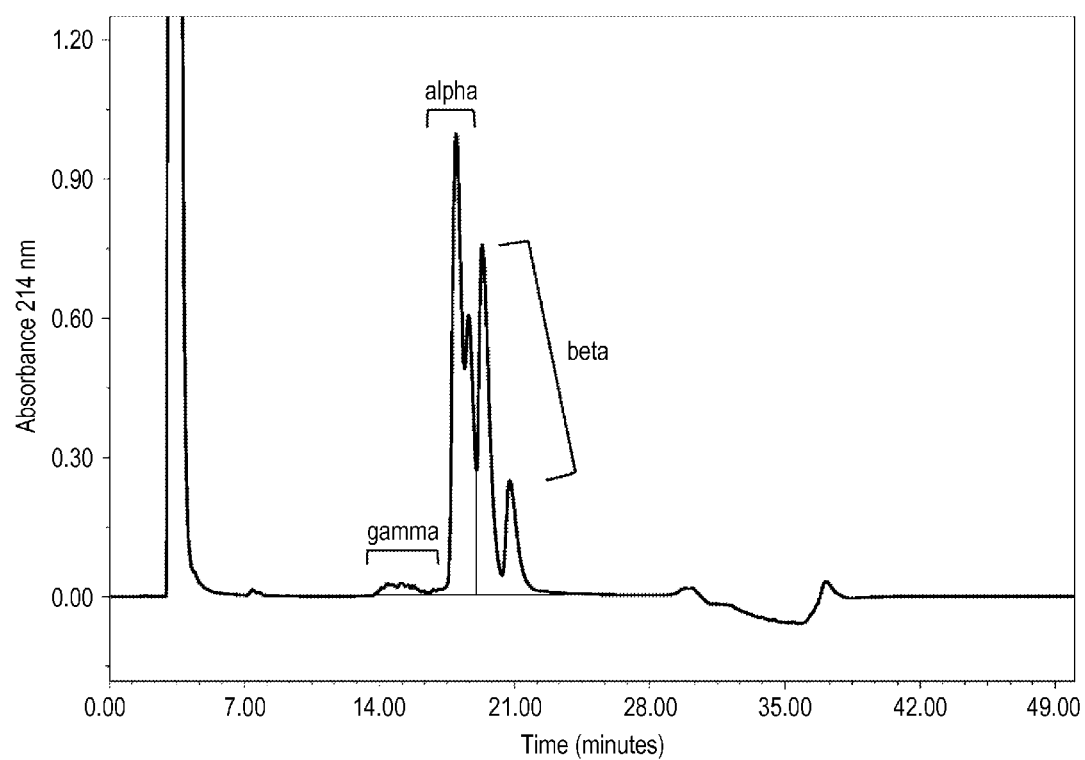
FIG. 3 provides an HPLC chromatogram of a purified preparation of intact FXa variant protein and demonstrates the existence in the preparation of different FXa variant protein isoforms.

Reversed phase high-performance liquid chromatography (RP-HPLC) was used to measure structural heterogeneity in one preparation of intact purified FXa variant protein. Purified protein was injected onto a reversed phase column and eluted with a gradient of acidified acetonitrile. Consistent with the observations from peptide mapping analysis, the FXa variant contained structural heterogeneity at the C-terminus of the heavy chain resulting in two major structural isoforms, alpha (terminating at $Lys^{399}$) and beta (terminating at $Lys^{386}$). An additional minor isoform, called gamma, was observed due to clipping of the heavy chain after $Lys^{281}$ or $Arg^{283}$. The HPLC chromatogram from these experiments is shown in FIG. 3.

The relative frequency of the major structural isoforms was consistent among seven preparations of purified FXa variant protein tested. In particular, based on relative peak distributions, the frequency of occurrence of the alpha isoform ranged from 54% to 74% (mean=66.9%, SD=7.0%), the frequency of occurrence of the beta isoform ranged from 24% to 42% (mean=31.4%, SD=6.5%), and the frequency of occurrence of the gamma isoform ranged from 1% to 3% (mean=2.0%, SD=0.8%).

Alpha and beta isoforms were purified using size-exclusion HPLC and tested for activity in a standard APTT-based clotting assay. The beta isoform demonstrated slightly lower activity (79%) compared to the alpha isoform (normalized as 100%). The activity of the minor gamma species was not tested.

Example 5

Structural Heterogeneity of Intact Protein Determined by Mass Spectroscopy

Figure 4:
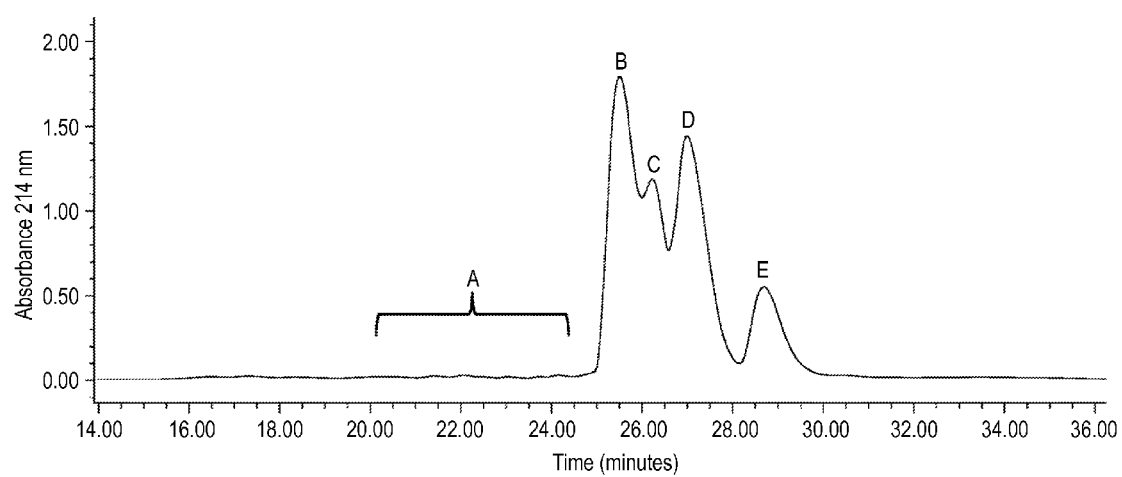
FIG. 4 provides an HPLC chromatogram of a purified preparation of intact FXa variant protein and demonstrates the existence in the preparation of different FXa variant protein isoforms. The preparation was also analyzed by mass spectrometry.
Figure 5:
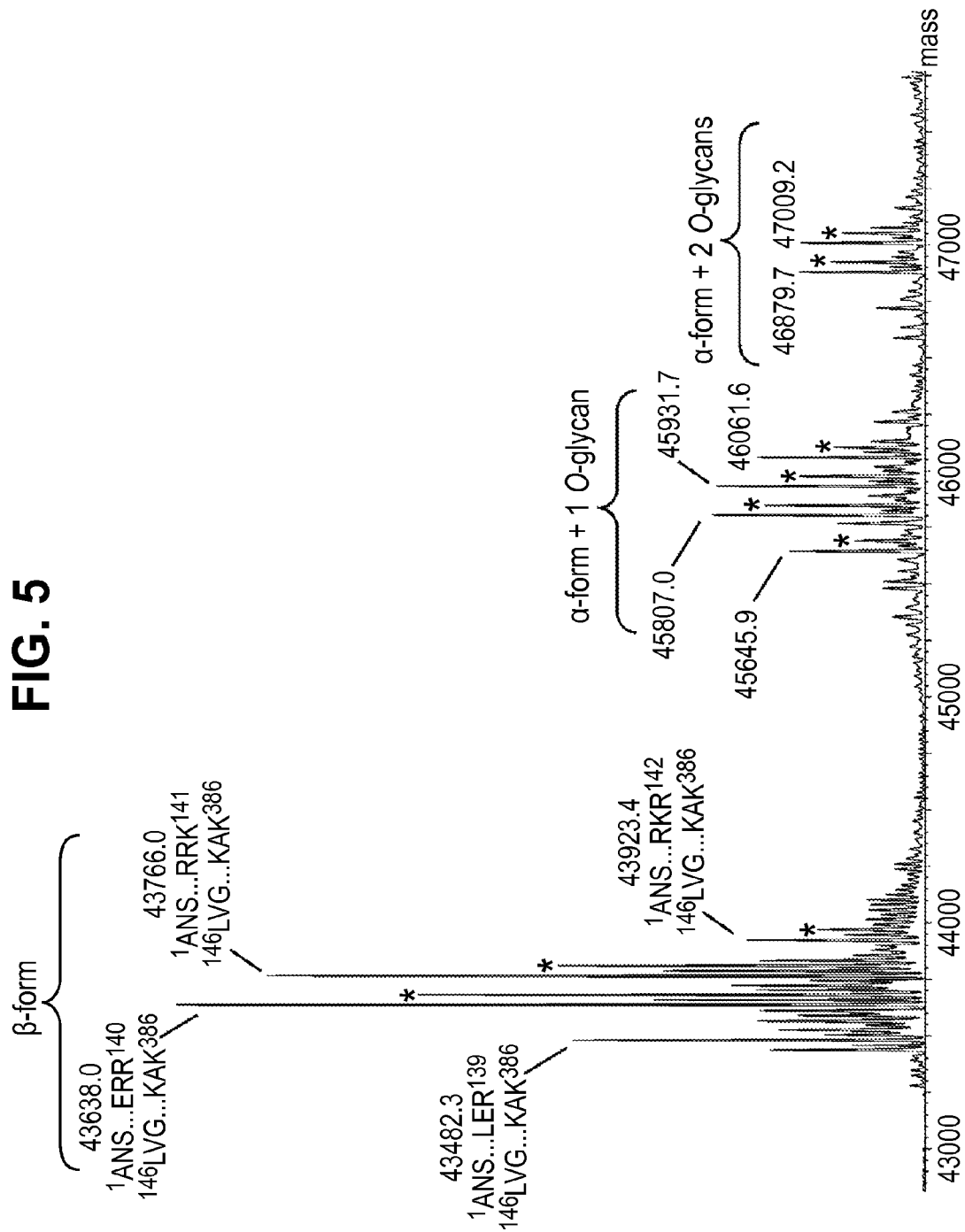
FIG. 5 provides the mass spectrum of intact FXa variant protein from a purified preparation. The mass spectrum confirms the existence of two major isoforms, alpha and beta, as well as extensive mass heterogeneity attributable to variable digestion at the PACE cleavage site and the presence of different types of post-translational modification. Major peaks are identified in the figure by their observed mass in daltons. Peak assignments based on the mass spectrum after RP-HPLC/ESI-QTOF MS analysis were used to confirm the amino acid sequence of protein isoforms and to identify certain post-translational modifications as described in Table 2 and elsewhere herein. Peaks labeled with "*" indicate the presence of 11 Gla residues in the light chain Gla domain.

Molecular mass ($M_r$) of intact FXa variant from one preparation of purified protein was analyzed by RP-HPLC followed by mass spectrometry using a high-resolution, hybrid quadrupole time-of-flight mass analyzer (ESI-QTOF MS). $M_r$ values were determined from the zero-charge mass spectra after deconvolution of the multiply charged data with Waters MaxEnt-1 software. The relative errors between the theoretical and observed major and minor mass values were all within ±60 ppm, which is consistent with the performance specifications of the Waters Q-ToF mass spectrometer. The HPLC chromatogram is shown in FIG. 4. The mass spectrum of intact FXa variant protein is shown in FIG. 5, and the peak assignments based on the mass spectrum are listed in Table 2 below. Amino acid numbering is based on FIG. 1A (SEQ ID NO:1). $^{1}ANS \ldots LER^{139}$ corresponds to SEQ ID NO:6; $^{1}ANS \ldots ERR^{140}$ corresponds to SEQ ID NO:7; $^{1}ANS \ldots RRK^{141}$ corresponds to SEQ ID NO:9; $^{1}ANS \ldots RKR^{142}$ corresponds to SEQ ID NO:11; $^{1}ANS \ldots KRR^{143}$ corresponds to SEQ ID NO:12; $^{146}LVG \ldots LPK^{384}$ corresponds to SEQ ID NO:45; $^{146}LVG \ldots KAK^{386}$ corresponds to SEQ ID NO:46; $^{146}LVG \ldots SPL^{398}$ corresponds to SEQ ID NO:14; and $^{146}LVG \ldots PLK^{399}$ corresponds to SEQ ID NO:3.

TABLE 2

| Light Chain | Heavy Chain | Heavy Chain O-glycan | Gla No. | Observed $M_r$ | Abundance |
|---|---|---|---|---|---|
| $^1$ANS ... ERR$^{140}$ | (β) $^{146}$LVG ... LPK$^{384}$ | 0 | 9 | 43394.6 | Trace |
| | | | 10 | 43438.6* | Minor |
| | | | 11 | 43482.3* | Major |
| $^1$ANS ... LER$^{139}$ | (β) $^{146}$LVG ... KAK$^{386}$ | 0 | 9 | 43438.6* | Minor |
| | | | 10 | 43482.3* | Major |
| $^1$ANS ... RRK$^{141}$ | (β) $^{146}$LVG ... LPK$^{384}$ | 0 | 9 | 43525.0 | Minor |
| | | | 10 | 43566.4 | Minor |
| | | | 11 | 43610.0 | Trace |
| $^1$ANS ... ERR$^{140}$ | (β) $^{146}$LVG ... KAK$^{386}$ | 0 | 9 | 43594.3 | Trace |
| | | | 10 | 43638.0 | Major |
| | | | 11 | 43681.1* | Major |
| $^1$ANS ... RKR$^{142}$ | (β) $^{146}$LVG ... LPK$^{384}$ | 0 | 9 | 43681.1* | Major |
| | | | 10 | 43722.3 | Minor |
| | | | 11 | 43766.0* | Major |
| $^1$ANS ... RRK$^{141}$ | (β) $^{146}$LVG ... KAK$^{386}$ | 0 | 9 | 43722.3 | Minor |
| | | | 10 | 43766.0* | Major |
| | | | 11 | 43810.2 | Major |
| $^1$ANS ... RKR$^{142}$ | (β) $^{146}$LVG ... KAK$^{386}$ | 0 | 9 | 43879.8* | Trace |
| | | | 10 | 43923.4* | Minor |
| | | | 11 | 43966.7 | Minor |
| $^1$ANS ... KRR$^{143}$ | (β) $^{146}$LVG ... LPK$^{384}$ | 0 | 9 | 43879.8* | Trace |
| | | | 10 | 43923.4* | Minor |
| | | | 11 | 43966.7 | Minor |
| $^1$ANS ... KRR$^{143}$ | (β) $^{146}$LVG ... KAK$^{386}$ | 0 | 10 | 44079.7 | Trace |
| $^1$ANS ... ERR$^{140}$ | (α) $^{146}$LVG ... SPL$^{398}$ | 1 + 1NeuAc-Gal | 10 | 45353.0 | Minor |
| $^1$ANS ... RRK$^{141}$ | (α) $^{146}$LVG ... SPL$^{398}$ | 1 + 1NeuAc-Gal | 10 | 45477.6* | Minor |
| $^1$ANS ... ERR$^{140}$ | (α) $^{146}$LVG ... PLK$^{399}$ | 1 + 1NeuAc-Gal | 10 | 45477.6* | Minor |
| $^1$ANS ... LER$^{139}$ | (α) $^{146}$LVG ... SPL$^{398}$ | 1 + 1NeuAc | 10 | 45356.0 | Trace |
| $^1$ANS ... ERR$^{140}$ | (α) $^{146}$LVG ... SPL$^{398}$ | 1 + 1NeuAc | 10 | 45514.4 | Minor |
| | | | 11 | 45557.5 | Minor |
| $^1$ANS ... LER$^{139}$ | (α) $^{146}$LVG ... SPL$^{398}$ | 1 + 2NeuAc | 9 | 45603.5 | Minor |
| | | | 10 | 45645.9 | Minor |
| | | | 11 | 45690.9 | Minor |
| $^1$ANS ... ERR$^{140}$ | (α) $^{146}$LVG ... SPL$^{398}$ | 1 + 2NeuAc | 10 | 45807.0 | Minor |
| | | | 11 | 45848.0 | Minor |
| $^1$ANS ... RRK$^{141}$ | (α) $^{146}$LVG ... SPL$^{398}$ | 1 + 2NeuAc | 9 | 45886.7 | Minor |
| | | | 10 | 45931.7 | Minor |
| | | | 11 | 45975.3 | Minor |
| $^1$ANS ... RRK$^{141}$ | (α) $^{146}$LVG ... PLK$^{399}$ | 1 + 2NeuAc | 9 | 46016.1 | Trace |
| | | | 10 | 46061.6 | Minor |
| | | | 11 | 46102.9 | Minor |
| $^1$ANS ... RKR$^{142}$ | (α) $^{146}$LVG ... SPL$^{398}$ | 1 + 2NeuAc | 11 | 46132.4 | Minor |
| $^1$ANS ... RRK$^{141}$ | (α) $^{146}$LVG ... PLK$^{399}$ | 1 + 2NeuAc | 9 | 46172.3* | Trace |
| $^1$ANS ... RKR$^{142}$ | (α) $^{146}$LVG ... PLK$^{399}$ | 1 + 2NeuAc | 9 | 46172.3* | Trace |
| | | | 10 | 46218.1 | Minor |
| | | | 11 | 46261.7 | Minor |
| $^1$ANS ... ERR$^{140}$ | (α) $^{146}$LVG ... PLK$^{399}$ | 2 + 2NeuAc | 10 | 46297.4* | Trace |
| $^1$ANS ... RRK$^{141}$ | (α) $^{146}$LVG ... SPL$^{398}$ | 2 + 2NeuAc | 10 | 46297.4* | Trace |
| $^1$ANS ... RRK$^{141}$ | (α) $^{146}$LVG ... PLK$^{399}$ | 2 + 2NeuAc | 10 | 46427.8 | Minor |
| | | | 11 | 46469.6 | Minor |
| $^1$ANS ... ERR$^{140}$ | (α) $^{146}$LVG ... PLK$^{399}$ | 2 + 3NeuAc | 10 | 46591.8* | Minor |
| | | | 11 | 46633.7* | Minor |
| $^1$ANS ... RRK$^{141}$ | (α) $^{146}$LVG ... SPL$^{398}$ | 2 + 3NeuAc | 10 | 46591.8* | Minor |
| | | | 11 | 46633.7* | Minor |
| $^1$ANS ... RRK$^{141}$ | (α) $^{146}$LVG ... PLK$^{399}$ | 2 + 3NeuAc | 10 | 46718.1 | Minor |
| | | | 11 | 46760.5 | Minor |
| $^1$ANS ... ERR$^{140}$ | (α) $^{146}$LVG ... SPL$^{398}$ | 2 + 4NeuAc | 11 | 46796.3 | Trace |
| $^1$ANS ... ERR$^{140}$ | (α) $^{146}$LVG ... PLK$^{399}$ | 2 + 4NeuAc | 10 | 46879.7 | Minor |
| | | | 11 | 46924.6 | Minor |
| $^1$ANS ... RRK$^{141}$ | (α) $^{146}$LVG ... SPL$^{398}$ | 2 + 4NeuAc | 10 | 46879.7 | Minor |
| | | | 11 | 46924.6 | Minor |
| $^1$ANS ... RRK$^{141}$ | (α) $^{146}$LVG ... PLK$^{399}$ | 2 + 4NeuAc | 9 | 46965.4 | Trace |
| | | | 10 | 47009.2 | Minor |
| | | | 11 | 47053.1 | Minor |
| $^1$ANS ... RKR$^{142}$ | (α) $^{146}$LVG ... PLK$^{399}$ | 2 + 4NeuAc | 10 | 47165.7 | Minor |

HPLC again demonstrated structural heterogeneity of the FXa variant protein (FIG. 4). The peaks labeled A correspond to gamma species. The peak labeled B correspond to the alpha form of the protein including two O-glycans. The peak labeled C correspond to the alpha form of the protein including one O-glycan. The peak labeled D corresponds to the beta form of the protein in which the heavy chain terminates with $K^{386}$. The peak labeled E corresponds to the beta form of the protein in which the heavy chain terminates with $K^{384}$.

Three regions were observed in the mass spectrum (FIG. 5). The first, at the lower end of the mass spectrum (left) corresponds to intact FXa variant protein containing the heavy chain beta isoform. This region also contains so-called major species which occur at greater prevalence compared to others based on relative peak intensity. The major species include those containing the beta form of the heavy chain terminating at $K^{386}$ in which the carboxy-terminal residue of the light chain was $R^{139}$, $R^{140}$, or $K^{141}$, apparently due to variable cleavage at PACE cleavage site. Species in which the light chain terminated at $R^{142}$, also apparently due to variable cleavage, were also present as a minor species. Among these major and minor species, the light chain included β-hydroxy $Asp^{63}$ and an O-linked hexose, as well as 10 or 11 Gla residues.

Two regions of greater mass also appear in the mass spectrum, both of which correspond to minor species of intact FXa variant protein containing the heavy chain alpha isoform (terminating at $L^{398}$ or $K^{399}$). One group of such species further includes a single O-glycan and a second group further includes two O-glycan post-translational modifications (center and right in FIG. 5, respectively).

Assignments expressly noted in FIG. 5 correspond to intact FXa variant protein species in which the light chain contained 10 Gla residues, β-hydroxy $Asp^{63}$ and O-linked glucose. Adjacent peaks in the spectrum labeled "*" represent species containing 11 Gla residues, which increases mass by 44.0 Da.

Table 2 lists the major and minor species identified from the mass spectrum described above, as well as numerous other minor and trace species identified from the mass spectrum data. In Table 2, species having the same observed $M_r$ value that could not be differentiated from a similar isobaric isoform in the table are denoted "*". Assignment of apparent abundance of the different species as major, minor and trace were based on relative peak intensities from the mass spectrum data. The column headed "O-glycan" lists the glycosylation status of the heavy chain of the various FXa variant protein species identified in the table. As discussed elsewhere herein, the light chain contains an O-linked hexose. In the table, "0" indicates presence of no O-linked glycans in the heavy chain; "1+1NeuAc" indicates presence of one core-1 mono-sialylated O-glycan; "1+1NeuAc–Gal" indicates the presence of one core-1 mono-sialylated O-glycan in which the terminal galactose (Gal) was not present; "1+2NeuAc" indicates presence of one core-1 di-sialylated O-glycan; "2+2NeuAc" indicates presence of two core-1 O-glycans one of which is di-sialylated or both of which are mono-sialylated; "2+3NeuAc" indicates presence of two core-1 O-glycans one of which is mono-sialylated and the other of which is di-sialylated; and "2+4NeuAc" indicates presence of two core-1 O-glycans each of which is di-sialylated.

Example 6

Structural Heterogeneity of Reduced and Alkylated Protein Determined by Mass Spectroscopy To confirm the analysis described above, purified intact FXa variant protein was reduced and alkylated to eliminate interchain and intrachain disulfide bonds. The separated light and heavy chains were then analyzed by RP-HPLC/ESI-QTOF MS to determine their amino acid structure and post-translational modification.

Figure 6:
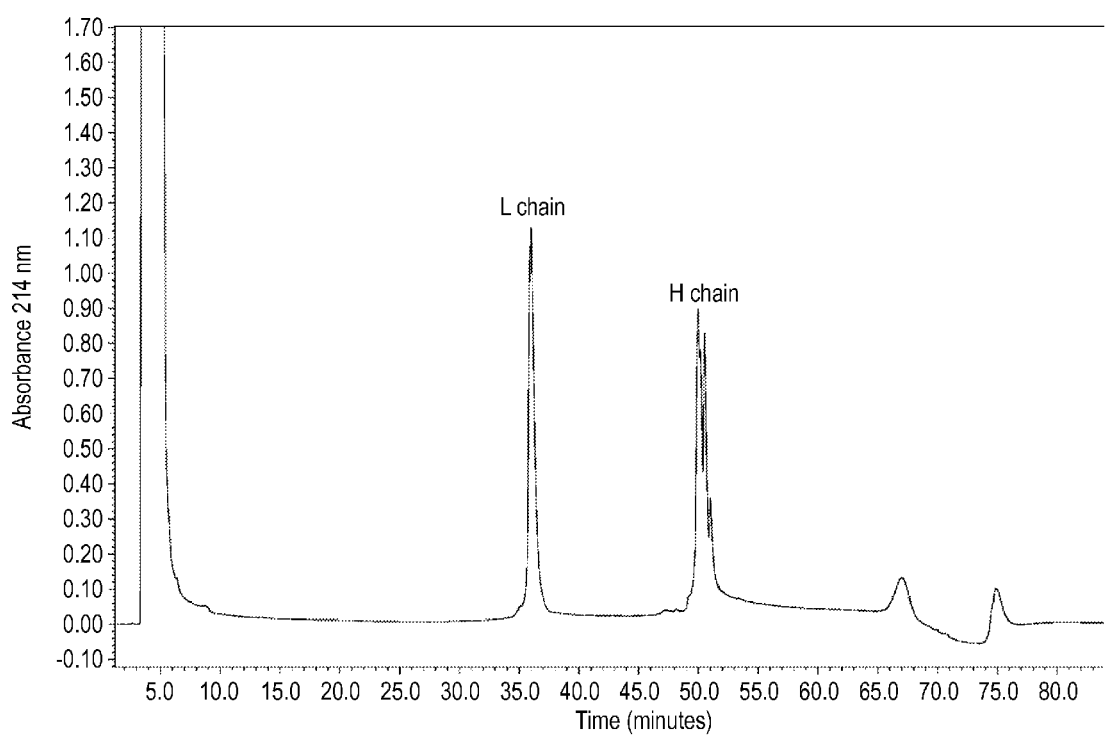
FIG. 6 provides an HPLC chromatogram of a purified preparation of FXa variant protein after reduction and alkylation to separate the light and heavy chains by eliminating interchain and intrachain disulfide bonds. The chromatogram demonstrates the existence of different FXa variant protein isoforms. The preparation was also analyzed by mass spectrometry.

The HPLC chromatogram is shown in FIG. 6 in which the light and heavy chains are labeled. The alpha and beta isoforms of the heavy chain elute as multiple chromatographic peaks. Trace levels of gamma species (beta heavy chain truncated after amino acid $K^{281}$ or $R^{283}$) were observed eluting just before the heavy chain at approximately 48-50 minutes in the chromatogram.

Figure 7A:
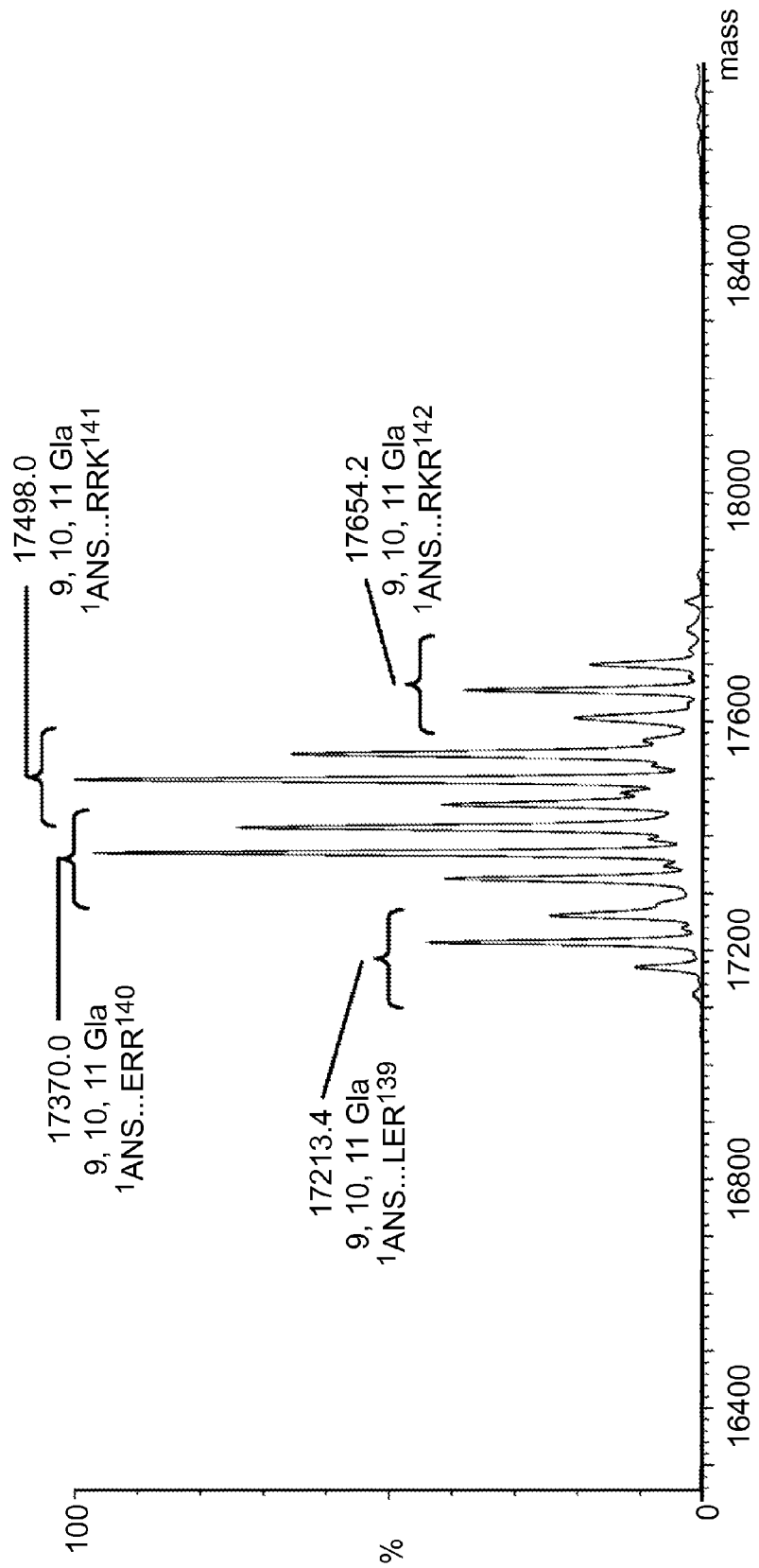
FIG. 7A provides the mass spectrum of FXa variant protein light chain after reduction and alkylation of a purified preparation of the protein. The mass spectrum demonstrates extensive mass heterogeneity attributable to variable digestion at the PACE cleavage site and presence of different types of post-translational modifications. Major peaks are identified in the figure by their observed mass in daltons. Peak assignments based on the mass spectrum after RP-HPLC/ESI-QTOF MS analysis were used to confirm the amino acid sequence of protein isoforms and to identify certain post-translational modifications as described in Table 3 and elsewhere herein.

The zero-charge mass spectrum of the light chain is shown in FIG. 7A and the species identified from the spectrum, including their relative abundance as major, minor or trace, are listed in Table 3 below. Amino acid numbering is based on FIG. 1A (SEQ ID NO:1). $^1$ANS . . . $LER^{139}$ corresponds to SEQ ID NO:6; $^1$ANS . . . $ERR^{140}$ corresponds to SEQ ID NO:7; $^1$ANS . . . $RRK^{141}$ corresponds to SEQ ID NO:9; $^1$ANS . . . $RKR^{142}$ corresponds to SEQ ID NO:11; and $^1$ANS . . . $KRR^{143}$ corresponds to SEQ ID NO:12.

TABLE 3

| Light Chain | Gla No. | Observed $M_r$ | Abundance |
| --- | --- | --- | --- |
| $^1$ANS . . . $LER^{139}$ | 9 | 17169.8 | Trace |
|  | 10 | 17213.4 | Minor |
|  | 11 | 17257.5 | Trace |
| $^1$ANS . . . $ERR^{140}$ | 9 | 17326.1 | Minor |
|  | 10 | 17370.0 | Major |
|  | 11 | 17413.7 | Major |
| $^1$ANS . . . $RRK^{141}$ | 9 | 17454.2 | Minor |
|  | 10 | 17498.0 | Major |
|  | 11 | 17542.0 | Major |
| $^1$ANS . . . $RKR^{142}$ | 9 | 17610.0 | Trace |
|  | 10 | 17654.2 | Minor |
|  | 11 | 17698.0 | Trace |
| $^1$ANS . . . $KRR^{143}$ | 10 | 17810.0 | Trace |

As seen with intact FXa variant protein, all light chain species were observed to include β-hydroxylation of $Asp^{63}$ and an O-linked hexose. Glutamic acid carboxylation in the Gla domain and PACE cleavage were variable, however, yielding light chain species with 9, 10 or 11 Gla residues and carboxy-terminal heterogeneity produced by ragged cleavage at the PACE site.

The zero-charge mass spectrum of the heavy chain is shown in FIG. 7B and the various species identified from the spectrum, including their relative abundance as major, minor or trace, are listed in Table 4 below. Amino acid numbering is based on FIG. 1A (SEQ ID NO: 1). $^{146}$LVG . . . $LPK^{384}$ corresponds to SEQ ID NO:45; $^{146}$LVG . . . $KAK^{386}$ corresponds to SEQ ID NO:46; $^{146}$LVG . . . $SPL^{398}$ corresponds to SEQ ID NO:14; and $^{146}$LVG . . . $PLK^{399}$ corresponds to SEQ ID NO:3.

TABLE 4

| Heavy chain | O-glycan | Observed $M_r$ | Abundance |
| --- | --- | --- | --- |
| (β) $^{146}$LVG . . . $LPK^{384}$ | 0 | 27484.2 | Minor |
| (β) $^{146}$LVG . . . $KAK^{386}$ | 0 | 27683.9 | Major |
| (α) $^{146}$LVG . . . $SPL^{398}$ | 1 core-1 | 29558.7 | Minor |
| (α) $^{146}$LVG . . . $SPL^{398}$ | 1 core-1 + 1 NeuAc | 29687.4 | Minor |
| (α) $^{146}$LVG . . . $SPL^{398}$ | 1 core-1 + 2 NeuAc | 29851.0 | Minor |
| (α) $^{146}$LVG . . . $PLK^{399}$ | 1 core-1 + 2 NeuAc | 29978.8 | Minor |
| (α) $^{146}$LVG . . . $PLK^{399}$ | 2 core-1 + 2 NeuAc | 30344.9 | Minor |
| (α) $^{146}$LVG . . . $PLK^{399}$ | 2 core-1 + 3 NeuAc | 30635.2 | Minor |
| (α) $^{146}$LVG . . . $SPL^{398}$ | 2 core-1 + 4 NeuAc | 30799.9 | Trace |
| (α) $^{146}$LVG . . . $PLK^{399}$ | 2 core-1 + 4 NeuAc | 30926.7 | Minor |

In the mass spectrum, the heavy chain was observed as three predominant regions corresponding to the beta and alpha isoforms. The observed $M_r$ of the most abundant heavy chain isoform (27683.9 Da) compared well with the theoretical mass of the beta heavy chain isoform (27684.3 Da; $^{146}$LVG . . . $KAK^{386}$) with all nine cysteine residues alkylated. Additional mass heterogeneity was due to variation in the carboxy-terminal residue and O-glycosylation of the alpha isoforms. Specifically, certain peaks corresponded to alpha isoforms terminating at $L^{398}$ or $K^{399}$, whereas other peaks corresponded to heavy chains carrying one or two core-1 O-glycans that were variably non-sialylated, mono-sialylated, or di-sialylated. In FIG. 7B, presence of the "*" indicates overalkylation of the heavy chain which is consistent with peaks observed by peptide mapping of the FXa variant protein (see Example 3).

The structural heterogeneity observed in the light and heavy chains after reduction and alkylation are consistent with the results observed using intact FXa variant protein.

Theoretical masses were calculated with PAWS software (2000.06.08, Genomic Solutions, Ann Arbor, Mich.). Observed masses were determined from the zero-charge mass spectra after deconvolution of the multiply charged data with Waters MaxEnt-1 software. The relative errors between the theoretical and observed major and minor mass values were all less than 60 ppm, which is consistent with the performance specifications of the Waters Q-ToF mass spectrometer for intact glycoprotein analysis. Assignments of major, minor and trace species were based on respective peak intensities, which correlate with isoform abundance.

Example 7

In Vitro Clotting Assay

Clotting activity of seven different preparations of FXa variant protein was determined using a one-stage clotting assay using Factor VIII deficient human plasma as substrate (APTT assay). Specific activity was determined by dividing clotting activity (mg/ml) by protein concentration (mg/ml). Average clotting activity across the preparations was 1.52 mg/ml with a standard deviation of 0.09. Average specific activity was 101.3% with a standard deviation of 5.9.

The present disclosure is not to be limited in scope by the specific embodiments described herein. Indeed, various modifications of the disclosure in addition to those described herein will become apparent to those skilled in the art from the foregoing description and accompanying figures. Such modifications are intended to fall within the scope of the appended claims.

Various references, including patent applications, patents, and technical publications, are cited herein. The disclosure of each such reference is hereby incorporated herein by reference in its entirety.

What is claimed is:

1. A composition with pro-coagulant activity comprising:
a first recombinant FXa variant protein wherein the light chain and heavy chain protein sequences respectively consist of amino acids 1 to 140 and 146 to 386 of the amino acid sequence of SEQ ID NO:1;
and a second recombinant FXa variant protein selected from the group consisting of:
(i) a recombinant FXa variant protein wherein the light chain and heavy chain protein sequences respectively consist of amino acids 1 to 139 and 146 to 386 of the amino acid sequence of SEQ ID NO:1,
(ii) a recombinant FXa variant protein wherein the light chain and heavy chain protein sequences respectively consist of amino acids 1 to 141 and 146 to 386 of the amino acid sequence of SEQ ID NO:1,
(iii) a recombinant FXa variant protein wherein the light chain and heavy chain protein sequences respectively consist of amino acids 1 to 142 and 146 to 386 of the amino acid sequence of SEQ ID NO:1,
(iv) a recombinant FXa variant protein wherein the light chain and heavy chain protein sequences respectively consist of amino acids 1 to 143 and 146 to 386 of the amino acid sequence of SEQ ID NO:1,
(v) a recombinant FXa variant protein wherein the light chain and heavy chain protein sequences respectively consist of amino acids 1 to 140 and 146 to 384 of the amino acid sequence of SEQ ID NO:1,
(vi) a recombinant FXa variant protein wherein the light chain and heavy chain protein sequences respectively consist of amino acids 1 to 141 and 146 to 384 of the amino acid sequence of SEQ ID NO:1,
(vii) a recombinant FXa variant protein wherein the light chain and heavy chain protein sequences respectively consist of amino acids 1 to 142 and 146 to 384 of the amino acid sequence of SEQ ID NO:1; and
(viii) a recombinant FXa variant protein wherein the light chain and heavy chain protein sequences respectively consist of amino acids 1 to 143 and 146 to 384 of the amino acid sequence of SEQ ID NO:1.

2. The composition of claim 1, wherein a light chain of at least one of said recombinant FXa variant proteins comprises β-hydroxy Asp$^{63}$ and an O-linked hexose.

3. The composition of claim 1, wherein a light chain of at least one of said recombinant FXa variant proteins comprises 10 Gla residues.

4. The composition of claim 1, wherein a light chain of at least one of said recombinant FXa variant proteins comprises 11 Gla residues.

5. The composition of claim 1, wherein a light chain of at least one of said recombinant FXa variant proteins comprises β-hydroxy Asp$^{63}$, an O-linked hexose, and 10 or 11 Gla residues.

6. The composition of claim 1, wherein said composition comprises:
(i) a first recombinant FXa variant protein wherein the light chain and heavy chain protein sequences respectively consist of amino acids 1 to 140 and 146 to 386 of the amino acid sequence of SEQ ID NO:1,
(ii) a second recombinant FXa variant protein wherein the light chain and heavy chain protein sequences respectively consist of amino acids 1 to 139 and 146 to 386 of the amino acid sequence of SEQ ID NO:1,
(iii) a third recombinant FXa variant protein wherein the light chain and heavy chain protein sequences respectively consist of amino acids 1 to 141 and 146 to 386 of the amino acid sequence of SEQ ID NO:1; and
(iv) a fourth recombinant FXa variant protein wherein the light chain and heavy chain protein sequences respectively consist of amino acids 1 to 142 and 146 to 386 of the amino acid sequence of SEQ ID NO:1.

7. The composition of claim 6, wherein a light chain of each of said first, second, third, and fourth recombinant FXa variant proteins comprises β-hydroxy Asp$^{63}$, an O-linked hexose, and at least 10 Gla residues.

8. The composition of claim 7, wherein a light chain of each of said first, third, and fourth recombinant FXa variant proteins comprises β-hydroxy Asp$^{63}$, an O-linked hexose, and 11 Gla residues.

9. A composition with pro-coagulant activity comprising:
a first recombinant FXa variant protein wherein the light chain and heavy chain protein sequence respectively consist of amino acids 1 to 140 and 146 to 398 of the amino acid sequence of SEQ ID NO:1;
and a second recombinant FXa variant protein selected from the group consisting of:
(i) a recombinant FXa variant protein wherein the light chain and heavy chain protein sequence respectively consist of amino acids 1 to 139 and 146 to 398 of the amino acid sequence of SEQ ID NO:1, (ii) a recombinant FXa variant protein wherein the light chain and heavy chain protein sequence respectively consist of amino acids 1 to 141 and 146 to 398 of the amino acid sequence of SEQ ID NO:1, (iii) a recombinant FXa variant protein wherein the light chain and heavy chain protein sequence respectively consist of amino acids 1 to 141 and 146 to 399 of the amino acid sequence of SEQ ID NO:1, (iv) a recombinant FXa variant protein wherein the light chain and heavy chain protein sequence respectively consist of amino acids 1 to 142 and 146 to 398 of the amino acid sequence of SEQ ID NO:1, (v) a recombinant FXa variant protein wherein the light chain and heavy chain protein sequences respectively consist of amino acids 1 to 140 and 146 to 399 of the amino acid sequence of SEQ ID NO:1, and (vi) a recombinant FXa variant protein wherein the light chain and heavy chain protein sequences respectively consist of amino acids 1 to 142 and 146 to 399 of the amino acid sequence of SEQ ID NO:1.

10. The composition of claim 9, wherein a light chain of at least one of said recombinant FXa variant proteins comprises β-hydroxy Asp$^{63}$ and an O-linked hexose.

11. The composition of claim 9, wherein a light chain of at least one of said recombinant FXa variant proteins comprises 10 Gla residues.

12. The composition of claim 9, wherein a light chain of at least one of said recombinant FXa variant proteins comprises 11 Gla residues.

13. The composition of claim 9, wherein a light chain of at least one of said recombinant FXa variant proteins comprises β-hydroxy Asp$^{63}$, an O-linked hexose, and 10 or 11 Gla residues.

14. The composition of claim 9, wherein a heavy chain of at least one of said recombinant FXa variant proteins comprises one core-1 O-linked glycan.

15. The composition of claim 14, wherein the core-1 O-linked glycan is mono-sialylated.

16. The composition of claim 14, wherein the core-1 O-linked glycan is di-sialylated.

17. The composition of claim 9, wherein a heavy chain of at least one of said recombinant FXa variant proteins comprises two core-1 O-linked glycans.

18. The composition of claim 17, wherein both core-1 O-linked glycans are mono-sialylated.

19. The composition of claim 17, wherein both core-1 O-linked glycans are di-sialylated.

20. The composition of claim 17, wherein one of said core-1 O-linked glycans is mono-sialylated and the second of said core-1 O-linked glycans is di-sialylated.

21. A composition with pro-coagulant activity comprising:
(i) a first recombinant FXa variant protein wherein the light chain and heavy chain protein sequences respectively consist of amino acids 1 to 140 and 146 to 398 of the amino acid sequence of SEQ ID NO: 1,
(ii) a second recombinant FXa variant protein wherein the light chain and heavy chain protein sequences respectively consist of amino acids 1 to 139 and 146 to 398 of the amino acid sequence of SEQ ID NO: 1,
(iii) a third recombinant FXa variant protein wherein the light chain and heavy chain protein sequences respectively consist of amino acids 1 to 141 and 146 to 398 of the amino acid sequence of SEQ ID NO: 1; and
(iv) a fourth recombinant FXa variant protein wherein the light chain and heavy chain protein sequences respectively consist of amino acids 1 to 141 and 146 to 399 of the amino acid sequence of SEQ ID NO: 1.

22. The composition of claim 21, wherein a light chain of each of said first, second, third, and fourth recombinant FXa variant proteins comprises β-hydroxy Asp$^{63}$, an O-linked hexose, and at least 10 Gla residues.

23. The composition of claim 22, wherein a light chain of each of said first, second, third, and fourth recombinant FXa variant proteins comprises β-hydroxy Asp$^{63}$, an O-linked hexose, and 11 Gla residues.

24. The composition of claim 21, wherein a heavy chain of each of said first, second, third, and fourth recombinant FXa variant proteins comprises one core-1 O-linked glycan.

25. The composition of claim 24, wherein the core-1 O-linked glycan is di-sialylated.

26. A composition with pro-coagulant activity comprising:
a first recombinant FXa variant protein wherein the light chain and heavy chain protein sequences respectively consist of amino acids 1 to 141 and 146 to 399 of the amino acid sequence of SEQ ID NO:1;
and a second recombinant FXa variant protein selected from the group consisting of:
(i) a recombinant FXa variant protein wherein the light chain and heavy chain protein sequences respectively consist of amino acids 1 to 140 and 146 o 399 of the amino acid sequence of SEQ ID NO:1; and
(ii) a recombinant FXa variant protein wherein the light chain and heavy chain protein sequences respectively consist of amino acids 1 to 141 and 146 to 398 of the amino acid sequence of SEQ ID NO:1.

27. The composition of claim 26, wherein a light chain of each of said first and second recombinant FXa variant proteins comprises β-hydroxy Asp$^{63}$, an O-linked hexose, and at least 10 Gla residues.

28. The composition of claim 27, wherein a light chain of each of said first and second recombinant FXa variant proteins comprises β-hydroxy Asp$^{63}$, an O-linked hexose, and 11 Gla residues.

29. The composition of claim 26, wherein a heavy chain of each of said first and second recombinant FXa variant proteins comprises two core-1 O-linked glycans.

30. The composition of claim 29, wherein both core-1 O-linked glycans are di-sialylated.

31. A composition with pro-coagulant activity comprising two or more recombinant FXa variant proteins selected from the group consisting of:
(a) a recombinant FXa variant protein wherein the light chain and heavy chain protein sequences respectively consist of amino acids 1 to 139 and 146 to 386 of the amino acid sequence of SEQ ID NO:1,
(b) a recombinant FXa variant protein wherein the light chain and heavy chain protein sequences respectively consist of amino acids 1 to 140 and 146 to 386 of the amino acid sequence of SEQ ID NO:1;
(c) a recombinant FXa variant protein wherein the light chain and heavy chain protein sequences respectively consist of amino acids 1 to 141 and 146 to 386 of the amino acid sequence of SEQ ID NO:1,
(d) a recombinant FXa variant protein wherein the light chain and heavy chain protein sequences respectively consist of amino acids 1 to 142 and 146 to 386 of the amino acid sequence of SEQ ID NO:1,
(e) a recombinant FXa variant protein wherein the light chain and heavy chain protein sequences respectively consist of amino acids 1 to 143 and 146 to 386 of the amino acid sequence of SEQ ID NO:1, (f) a recombinant FXa variant protein wherein the light chain and heavy chain protein sequences respectively consist of amino acids 1 to 140 and 146 to 384 of the amino acid sequence of SEQ ID NO:1, (g) a recombinant FXa variant protein wherein the light chain and heavy chain protein sequences respectively consist of amino acids 1 to 141 and 146 to 384 of the amino acid sequence of SEQ ID NO:1, (h) a recombinant FXa variant protein wherein the light chain and heavy chain protein sequences respectively consist of amino acids 1 to 142 and 146 to 384 of the amino acid sequence of SEQ ID NO:1, and (i) a recombinant FXa variant protein wherein the light chain and heavy chain protein sequences respectively consist of amino acids 1 to 143 and 146 to 384 of the amino acid sequence of SEQ ID NO:1.

32. The composition of claim 31, wherein the light chains of said recombinant FXa variant proteins comprise β-hydroxy Asp$^{63}$ and an O-linked hexose.

33. The composition of claim 31, wherein the light chains of said recombinant FXa variant proteins comprise β-hydroxy Asp$^{63}$, an O-linked hexose, and 10 or 11 Gla residues.

34. The composition of claim 31, comprising 3, 4, 5, 6, 7, 8, or all 9 recombinant FXa variant proteins selected from among (a)-(i).

35. A composition with pro-coagulant activity comprising two or more recombinant FXa variant proteins selected from the group consisting of:
(a) a recombinant FXa variant protein wherein the light chain and heavy chain protein sequence respectively consist of amino acids 1 to 139 and 146 to 398 of the amino acid sequence of SEQ ID NO:1,
(b) a recombinant FXa variant protein wherein the light chain and heavy chain protein sequence respectively consist of amino acids 1 to 140 and 146 to 398 of the amino acid sequence of SEQ ID NO:1;
(c) a recombinant FXa variant protein wherein the light chain and heavy chain protein sequence respectively consist of amino acids 1 to 141 and 146 to 398 of the amino acid sequence of SEQ ID NO:1,
(d) A recombinant FXa variant protein wherein the light chain and heavy chain protein sequence respectively consist of amino acids 1 to 142 and 146 to 398 of the amino acid sequence of SEQ ID NO:1,
(e) a recombinant FXa variant protein wherein the light chain and heavy chain protein sequences respectively consist of amino acids 1 to 140 and 146 to 399 of the amino acid sequence of SEQ ID NO:1,
(f) a recombinant FXa variant protein wherein the light chain and heavy chain protein sequences respectively consist of amino acids 1 to 141 and 146 to 399 of the amino acid sequence of SEQ ID NO:1, and
(g) a recombinant FXa variant protein wherein the light chain and heavy chain protein sequences respectively consist of amino acids 1 to 142 and 146 to 399 of the amino acid sequence of SEQ ID NO:1.

36. The composition of claim 35, wherein the light chains of said recombinant FXa variant proteins comprise β-hydroxy Asp$^{63}$ and an O-linked hexose.

37. The composition of claim 35, wherein the light chains of said recombinant FXa variant proteins comprise β-hydroxy Asp$^{63}$, an O-linked hexose, and 10 or 11 Gla residues.

38. The composition of claim 35, wherein the heavy chains of said recombinant FXa variant proteins comprise one or two core-1 O-linked glycans.

39. The composition of claim 38, wherein at least one of said core-1 O-linked glycans is mono-sialylated or di-sialylated.

40. The composition of claim 35, comprising 3, 4, 5, 6, or all 7 recombinant FXa variant proteins selected from among (a)-(g).

41. A composition with pro-coagulant activity comprising:
(a) a recombinant FXa variant protein wherein the light chain and heavy chain protein sequences respectively consist of amino acids 1 to 139 and 146 to 386 of the amino acid sequence of SEQ ID NO:1,
(b) a recombinant FXa variant protein wherein the light chain and heavy chain protein sequences respectively consist of amino acids 1 to 140 and 146 to 386 of the amino acid sequence of SEQ ID NO:1;
(c) a recombinant FXa variant protein wherein the light chain and heavy chain protein sequences respectively consist of amino acids 1 to 141 and 146 to 386 of the amino acid sequence of SEQ ID NO:1,
(d) a recombinant FXa variant protein wherein the light chain and heavy chain protein sequences respectively consist of amino acids 1 to 142 and 146 to 386 of the amino acid sequence of SEQ ID NO:1,
(e) a recombinant FXa variant protein wherein the light chain and heavy chain protein sequences respectively consist of amino acids 1 to 143 and 146 to 386 of the amino acid sequence of SEQ ID NO:1,
(f) a recombinant FXa variant protein wherein the light chain and heavy chain protein sequences respectively consist of amino acids 1 to 140 and 146 to 384 of the amino acid sequence of SEQ ID NO:1,
(g) a recombinant FXa variant protein wherein the light chain and heavy chain protein sequences respectively consist of amino acids 1 to 141 and 146 to 384 of the amino acid sequence of SEQ ID NO:1,
(h) a recombinant FXa variant protein wherein the light chain and heavy chain protein sequences respectively consist of amino acids 1 to 142 and 146 to 384 of the amino acid sequence of SEQ ID NO:1,
(i) a recombinant FXa variant protein wherein the light chain and heavy chain protein sequences respectively consist of amino acids 1 to 143 and 146 to 384 of the amino acid sequence of SEQ ID NO:1,
(j) a recombinant FXa variant protein wherein the light chain and heavy chain protein sequence respectively consist of amino acids 1 to 139 and 146 to 398 of the amino acid sequence of SEQ ID NO:1,
(k) a recombinant FXa variant protein wherein the light chain and heavy chain protein sequence respectively consist of amino acids 1 to 140 and 146 to 398 of the amino acid sequence of SEQ ID NO:1;
(l) a recombinant FXa variant protein wherein the light chain and heavy chain protein sequence respectively consist of amino acids 1 to 141 and 146 to 398 of the amino acid sequence of SEQ ID NO:1,
(m) a recombinant FXa variant protein wherein the light chain and heavy chain protein sequence respectively consist of amino acids 1 to 142 and 146 to 398 of the amino acid sequence of SEQ ID NO:1,
(n) a recombinant FXa variant protein wherein the light chain and heavy chain protein sequences respectively consist of amino acids 1 to 140 and 146 to 399 of the amino acid sequence of SEQ ID NO:1,
(o) a recombinant FXa variant protein wherein the light chain and heavy chain protein sequences respectively consist of amino acids 1 to 141 and 146 to 399 of the amino acid sequence of SEQ ID NO:1, and (p) a recombinant FXa variant protein wherein the light chain and heavy chain protein sequences respectively consist of amino acids 1 to 142 and 146 to 399 of the amino acid sequence of SEQ ID NO:1.

42. The composition of claim 41, wherein the light chains of said recombinant FXa variant proteins comprise β-hydroxy Asp$^{63}$, an O-linked hexose, and 10 or 11 Gla residues.

43. The composition of claim 41, wherein the heavy chains of said recombinant FXa variant proteins comprise one or two core-1 O-linked glycans.

44. The composition of claim 42, wherein at least one of said core-1 O-linked glycans is mono-sialylated or di-sialylated.

45. The composition of claim 31 further comprising two or more recombinant FXa variant proteins selected from the group consisting of:

(a) a recombinant FXa variant protein wherein the light chain and heavy chain protein sequence respectively consist of amino acids 1 to 139 and 146 to 398 of the amino acid sequence of SEQ ID NO:1, (b) a recombinant FXa variant protein wherein the light chain and heavy chain protein sequence respectively consist of amino acids 1 to 140 and 146 to 398 of the amino acid sequence of SEQ ID NO:1;

(c) a recombinant FXa variant protein wherein the light chain and heavy chain protein sequence respectively consist of amino acids 1 to 141 and 146 to 398 of the amino acid sequence of SEQ ID NO:1, (d) A recombinant FXa variant protein wherein the light chain and heavy chain protein sequence respectively consist of amino acids 1 to 142 and 146 to 398 of the amino acid sequence of SEQ ID NO:1, (e) a recombinant FXa variant protein wherein the light chain and heavy chain protein sequences respectively consist of amino acids 1 to 140 and 146 to 399 of the amino acid sequence of SEQ ID NO:1, (f) a recombinant FXa variant protein wherein the light chain and heavy chain protein sequences respectively consist of amino acids 1 to 141 and 146 to 399 of the amino acid sequence of SEQ ID NO:1, and (g) a recombinant FXa variant protein wherein the light chain and heavy chain protein sequences respectively consist of amino acids 1 to 142 and 146 to 399 of the amino acid sequence of SEQ ID NO:1.

* * * * *